(12) United States Patent
Yang et al.

(10) Patent No.: US 11,180,536 B2
(45) Date of Patent: Nov. 23, 2021

(54) ANTIBODIES TO ROYALACTIN AND USES THEREOF

(71) Applicant: WYL Sciences Inc., Newport Beach, CA (US)

(72) Inventors: George P. Yang, Newport Beach, CA (US); Kevin C. Wang, Newport Beach, CA (US); Derrick C. Wan, Newport Beach, CA (US)

(73) Assignee: WYL SCIENCES INC., Newport Beach, CA (US)

( * ) Notice: Subject to any disclaimer, the term of this patent is extended or adjusted under 35 U.S.C. 154(b) by 0 days.

(21) Appl. No.: 16/604,123

(22) PCT Filed: Apr. 11, 2018

(86) PCT No.: PCT/US2018/027175
§ 371 (c)(1),
(2) Date: Oct. 9, 2019

(87) PCT Pub. No.: WO2018/191422
PCT Pub. Date: Oct. 18, 2018

(65) Prior Publication Data
US 2020/0377560 A1    Dec. 3, 2020

Related U.S. Application Data

(60) Provisional application No. 62/485,263, filed on Apr. 13, 2017.

(51) Int. Cl.
| | |
|---|---|
| *C07K 1/22* | (2006.01) |
| *C07K 16/18* | (2006.01) |
| *C07K 14/435* | (2006.01) |
| *A23L 21/20* | (2016.01) |

(52) U.S. Cl.
CPC .......... *C07K 14/43572* (2013.01); *C07K 1/22* (2013.01); *A23L 21/20* (2016.08); *C07K 16/18* (2013.01); *C07K 2317/565* (2013.01)

(58) Field of Classification Search
CPC ..... C07K 14/43572; C07K 1/22; A23L 21/20; A61K 35/644
See application file for complete search history.

(56) References Cited

FOREIGN PATENT DOCUMENTS

| CN | 103059135 A | * | 4/2013 |
|---|---|---|---|
| JP | 2008-137968 | | 6/2008 |
| JP | 2012-202966 | | 10/2012 |
| WO | WO 2015/164981 A1 | | 11/2015 |

OTHER PUBLICATIONS

International Preliminary Report On Patentability dated Oct. 15, 2019 in International Application No. PCT/US2018/027175.
Suarez et al., One-Step Purification Of Nisin A By Immunoaffinity Chromatography, Applied And Environmental Microbiology, vol. 63, No. 12, pp. 4990-4992, 1997.
International Search Report and Written Opinion dated Jul. 9, 2018 in Application No. PCT/US2018/027175.
Reo et al., "A rapid method to isolate soluble royal jelly proteins", Food Chemistry, vol. 134, No. 4, pp. 2332-2337, Oct. 15, 2012.
Yamaguchi et al., "Quantification of major royal jelly protein 1 in fresh royal jelly by indirect enzyme-linked immunosorbent assay", Biosci Biotechnol Biochem, vol. 77, No. 6, pp. 1310-1312, Jun. 7, 2013.
Chothia et al., Canonical structures for the hypervariable regions of immunoglobulins, Journal of Molecular Biology, vol. 196, No. 4, pp. 901-917, 1987.
Clackson et al., In vitro selection from protein and peptide libraries, Trends Biotechnology, vol. 12, No. 5, pp. 173-184, 1994.
Greenfield, Chapter 7, Generating Monoclonal Antibodies, Antibodies: A Laboratory Manual, Second Edition, Cold Spring Harbor Laboratory Press, 2014.
Janeway, Chapter 3, Antigen Recognition by B-Cell and T-Cell Receptors, Immunobiology Fifth Edition, New York, Garland Science, 2001.
Kabat et al., Table of Contents of Sequences of Proteins of Immunological Interest, 5th Edition, Public Health Service, National Institutes of Health, 1991.
Martin et al., Modeling antibody hypervariable loops: A combined algorithm, Proceedings of the National Academy of Sciences of the United States of America, vol. 8, pp. 9268-9272, 1989.

* cited by examiner

*Primary Examiner* — Daniel E Kolker
*Assistant Examiner* — James L Rogers
(74) *Attorney, Agent, or Firm* — Knobbe, Martens, Olson & Bear LLP

(57) ABSTRACT

Antibodies specific for royalactin (RA) can be used in methods for purifying royalactin, including native royalactin. These methods produce can produce compositions enriched for native royalactin. The purified royalactin can be used to produce cosmetic products that include native royalactin. An isolated nucleic acid encodes a monoclonal antibody that binds specifically to royalactin.

10 Claims, 9 Drawing Sheets

Specification includes a Sequence Listing.

FIG. 1A

MRJP1/Royalactin coding sequence in honeybees (GenBank: AF000633.1)

```
ATGACAAGATTGTTTATGCTGGTATGCCTTGGCATAGTTTGTCAAGGTACGACAGGCAACATTC
TTCGAGGAGAGTCTTTAAACAAATCATTACCCATCCTTCACGAATGGAAATTCTTTGATTATGA
TTTCGGTAGCGATGAAAGAAGACAAGATGCAATTCTATCTGGCGAATACGACTACAAGAATAAT
TATCCATCCGACATTGACCAATGGCATGATAAGATTTTTGTCACCATGCTGAGATACAATGGCG
TACCTTCCTCTTTGAACGTGATATCTAAAAAGGTCGGTGATGGTGGTCCTCTTCTACAACCTTA
TCCCGATTGGTCGTTTGCTAAATATGACGATTGCTCTGGAATCGTGAGCGCCTCAAAACTTGCG
ATCGACAAATGCGACAGATTGTGGGTTCTGGACTCAGGTCTTGTCAATAATACTCAACCCATGT
GTTCTCCAAAACTGCTCACCTTTGATCTGACTACCTCGCAATTGCTCAAGCAAGTTGAAATACC
ACATGATGTTGCCGTAAATGCCACTACAGGAAAGGGAAGATTATCATCTCTAGCTGTTCAATCT
TTAGATTGCAATACAAATAGCGATACTATGGTGTACATAGCAGACGAGAAAGGTGAAGGTTTAA
TCGTGTATCATAATTCTGATGATTCCTTCCATCGATTGACTTCCAACACTTTCGATTACGATCC
TAAATTTACCAAAATGACGATCGATGGAGAAAGTTACACAGCCCAAGATGGAATTTCTGGAATG
GCTCTTAGTCCCATGACTAACAATCTCTATTACAGTCCTGTAGCTTCCACCAGTTTGTATTATG
TTAACACGGAACAATTCAGAACATCCGATTATCAACAGAATGACATACATTACGAAGGAGTCCA
AAATATTTTGGATACCCAATCGTCCGCTAAAGTAGTATCAAAGAGTGGCGTTCTCTTCTTCGGA
TTGGTGGGCGATTCAGCTCTTGGCTGCTGGAACGAACATCGAACACTTGAAAGACACAATATCC
GTACCGTCGCTCAAAGTGATGAGACTCTTCAAATGATCGCTAGCATGAAGATTAAGGAAGCTCT
NCCACACGTGCCTATATTCGATAGGTATATAAACCGTGAATACATATTGGTTTTAAGTAACAAA
ATGCAAAAAATGGTGAATAATGACTTCAACTTCGACGATGTTAACTTCAGAATTATGAACGCGA
ATGTAAACGAATTGATATTGAACACTCGTTGCGAAAATCCCGATAATGATCGAACACCTTTCAA
AATTTCAATCCATTTGTAA     (SEQ ID NO: 1)
```

FIG. 1B

MRJP1/Royalactin amino acid sequence in honeybees

```
MTRLFMLVCLGIVCQGTTGNILRGESLNKSLPILHEWKFFDYDFGSDERRQDAILSGEYDYKNN
YPSDIDQWHDKIFVTMLRYNGVPSSLNVISKKVGDGGPLLQPYPDWSFAKYDDCSGIVSASKLA
IDKCDRLWVLDSGLVNNTQPMCSPKLLTFDLTTSQLLKQVEIPHDVAVNATTGKGRLSSLAVQS
LDCNTNSDTMVYIADEKGEGLIVYHNSDDSFHRLTSNTFDYDPKFTKMTIDGESYTAQDGISGM
ALSPMTNNLYYSPVASTSLYYVNTEQFRTSDYQQNDIHYEGVQNILDTQSSAKVVSKSGVLFFG
LVGDSALGCWNEHRTLERHNIRTVAQSDETLQMIASMKIKEAXPHVPIFDRYINREYILVLSNK
MQKMVNNDFNFDDVNFRIMNANVNELILNTRCENPDNDRTPFKISIHL (SEQ ID NO: 2)
```

FIG. 2A

Flag-Royalactin-His coding sequence

ATGGAATGGAGCTGGGTCTTTCTCTTCTTCCTGTCAGTAACGACTGGTGTCCACTCCGATTACA
AGGACGACGATGACAAGAACATTCTGCGTGGGGAATCCCTGAACAAGTCATTGCCTATCCTTCA
TGAATGGAAATTCTTTGATTATGATTTTGGTTCCGACGAACGACGGCAGGACGCCATCCTCTCT
GGAGAATATGATTACAAAAACAACTACCCTTCTGATATCGACCAGTGGCACGATAAGATTTTTG
TCACCATGCTGCGGTACAATGGAGTTCCCTCTTCACTGAACGTCATCAGTAAGAAGGTGGGCGA
CGGAGGACCCCTGCTCCAGCCATATCCTGATTGGTCTTTCGCTAAGTACGACGACTGTTCTGGA
ATCGTCTCCGCTTCTAAGCTGGCCATTGACAAGTGTGATCGGTTGTGGGTCCTGGATTCAGGGT
TGGTGAACAATACCCAGCCCATGTGCTCTCCTAAGCTGCTGACCTTCGACCTCACCACCAGCCA
GTTGCTCAAGCAGGTGGAGATTCCCCACGACGTCGCTGTGAACGCTACCACAGGCAAGGGCCGC
TTGAGCAGCCTTGCTGTGCAAAGCCTGGACTGCAACACCAATTCAGATACTATGGTGTACATCG
CAGACGAAAAGGGTGAAGGTCTGATTGTCTACCATAACTCAGACGATAGTTTTCATAGACTGAC
CTCCAACACATTCGATTATGACCCCAAGTTCACTAAGATGACTATTGACGGTGAGTCATACACT
GCCCAGGACGGGATTTCCGGTATGGCACTGTCACCTATGACAAATAACCTGTATTATTCTCCCG
TTGCAAGCACTTCTCTGTACTACGTGAACACTGAGCAATTCAGGACCAGCGACTATCAACAGAA
TGATATCCATTACGAGGGAGTCCAGAACATCCTTGACACTCAGTCCTCTGCCAAGGTAGTTAGC
AAGAGTGGAGTATTGTTTTCGGCCTGGTTGGCGACAGTGCTTTGGGATGTTGGAATGAACATC
GGACCCTGGAACGTCATAACATTCGCACTGTGGCCCAATCTGACGAGACTCTTCAGATGATCGC
CTCTATGAAGATAAAGGAGGCCTTGCCCCACGTCCCTATCTTCGACAGGTATATCAACCGTGAA
TATATACTGGTGCTCTCAAATAAGATGCAGAAAATGGTTAATAATGATTTCAATTTTGACGATG
TGAATTTTAGGATCATGAACGCAAACGTTAATGAACTGATCTTGAATACCCGTTGTGAGAATCC
CGACAACGATAGGACACCCTTTAAGATTTCTATTCACCTGCACCACCATCATCACCATCACCAC
CATCACTAG (SEQ ID NO: 3)

FIG. 2B

Flag-Royalactin-His amino acid sequence

MEWSWVFLFFLSVTTGVHSDYKDDDDKNILRGESLNKSLPILHEWKFFDYDFGSDERRQDAILS
GEYDYKNNYPSDIDQWHDKIFVTMLRYNGVPSSLNVISKKVGDGGPLLQPYPDWSFAKYDDCSG
IVSASKLAIDKCDRLWVLDSGLVNNTQPMCSPKLLTFDLTTSQLLKQVEIPHDVAVNATTGKGR
LSSLAVQSLDCNTNSDTMVYIADEKGEGLIVYHNSDDSFHRLTSNTFDYDPKFTKMTIDGESYT
AQDGISGMALSPMTNNLYYSPVASTSLYYVNTEQFRTSDYQQNDIHYEGVQNILDTQSSAKVVS
KSGVLFFGLVGDSALGCWNEHRTLERHNIRTVAQSDETLQMIASMKIKEALPHVPIFDRYINRE
YILVLSNKMQKMVNNDFNFDDVNFRIMNANVNELILNTRCENPDNDRTPFKISIHLHHHHHHHH
HH (SEQ ID NO: 4)

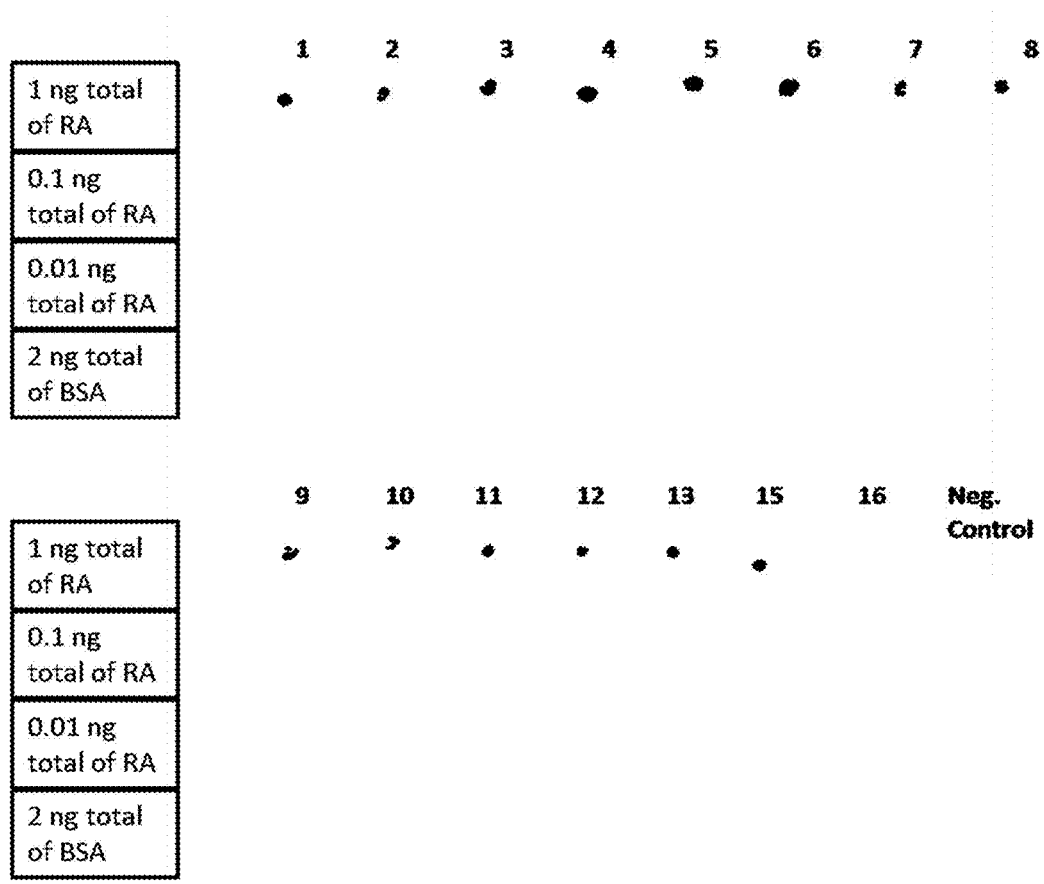

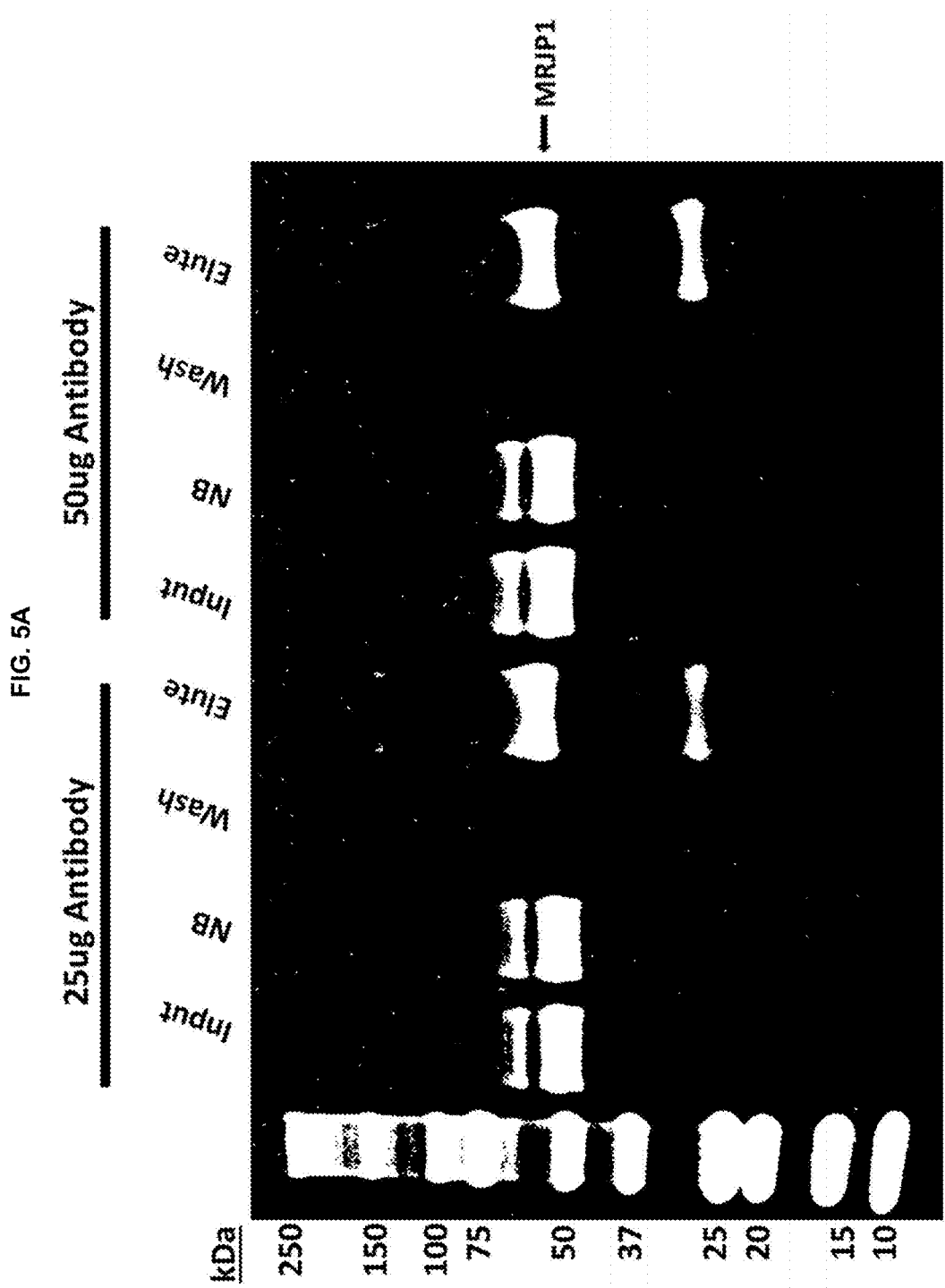

FIG. 6A

Clone 4G6C5 – Heavy Chain Variable Region (nucleic acid)

H-17,20,21,23,25

GTGATGCTGGTGGAATCTGGGGGAGGCTTAGTGAAGCCTGGAGGGTCCCTGAAACTCTCCTGTG
CAGCCTCTGGATTCACTTTCAGTAGGTATGCCATGTCTTGGAATCGCCAGACTCCGGAGAAGAG
GCTGGAGTGGGTCGCAACAATTAGTCCTGGTGGTGGTTACATATACTATTCAGACAGTGTGAAG
GGGCGATTCACCATCTCCAGAGACAATGCCAGGAACACCCTGTATCTGCAAATGAGCAGTCTGA
GGTCTGAGGACACGGCCATGTATTACTGTGCAGGGGACTATGTTGACTATTGGGGCCAAGGCAC
CACTCTCACAGTCTCCTCA (SEQ ID NO: 5)

FIG. 6B

Clone 4G6C5 – Heavy Chain Variable Region (translated polypeptide)

VMLVESGGGLVKPGGSLKLSCAASGFTFSRYAMSWNRQTPEKRLEWVATISPGGGYIYYSDSVK
GRFTISRDNARNTLYLQMSSLRSEDTAMYYCAGDYVDYWGQGTTLTVSS    (SEQ ID NO: 6)

FIG. 6C

Clone 4G6C5 – Light Chain Variable Region (nucleic acid)

K- 18,20,21,22,23

GATGTTGTGATGACCCAGACTCCACTCACTTTGTCGGTTACCACTGGACAACCAGCCTCCATCT
CTTGCAAGTCAAGTCAGAGCCTCTTAAATAGTGATGGAAAGACATTTTTGAATTGGTTGTTACA
GAGGCCAGGGCAGTCTCCAAAGCGCCTAATCTATCTGGTGTCTAAACTGGACTCTGGAGTCCCT
GACAGGTTCACTGGCAGTGGATCAGGGACAGATTTCACACTGAAAATCAGCAGAGTGGAGGCTG
AGGATTTGGGAGTTTATTATTGCTGGCAAGGTACACATTTTCCATACACGTTCGGAGGGGGGAC
CAAGCTGGAAATAAAACGG    (SEQ ID NO: 7)

FIG. 6D

Clone 4G6C5 – Light Chain Variable Region (translated polypeptide)

DVVMTQTPLTLSVTTGQPASISCKSSQSLLNSDGKTFLNWLLQRPGQSPKRLIYLVSKLDSGVP
DRFTGSGSGTDFTLKISRVEAEDLGVYYCWQGTHFPYTFGGGTKLEIKR (SEQ ID NO: 8)

US 11,180,536 B2

ANTIBODIES TO ROYALACTIN AND USES THEREOF

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. The present application claims the benefit of U.S. Provisional App. No. 62/485,263, filed Apr. 13, 2017, which is hereby incorporated by reference in its entirety.

REFERENCE TO SEQUENCE LISTING, TABLE, OR COMPUTER PROGRAM LISTING

The present application is being filed along with a Sequence Listing in electronic format. The Sequence Listing is provided as a file entitled WYLS001WO.TXT, created and last modified on Apr. 5, 2018, which is 14,267 bytes in size. The information in the electronic format of the Sequence Listing is incorporated herein by reference in its entirety.

FIELD

Some embodiments herein relate generally to antibodies specific for royalactin (RA), and methods of using such antibodies, for example to purify native royalactin.

SUMMARY

Some aspects include methods for purifying native royalactin. The methods can comprise solubilizing a biological matter comprising native royalactin, for example in an aqueous solution. The method can comprise contacting the solution comprising the solubilized biological matter (which, by way of example can be an aqueous solution, as noted above) with a monoclonal antibody immobilized on a substrate, in which the monoclonal antibody binds specifically to the amino acid sequence of SEQ ID NO: 2, and in which the monoclonal antibody binds to the native royalactin. The method can comprise separating the monoclonal antibody bound to native royalactin from the solution, for example via washing. The method can further comprise removing the bound native royalactin from the monoclonal antibody, for example by elution, thus purifying native royalactin. In some embodiments, the method further comprises preparing a composition comprising purified native royalactin. The composition can comprise lyophilized native royalactin, or can be part of a cosmetic product comprising the native royalactin, for example a topical cosmetic product. Accordingly, in some embodiments, the method produces a composition enriched for native royalactin. The composition can comprise at least 1% (w/w) native royalactin, for example, at least 1%, 2%, 3%, 4%, 5%, 6%, 7%, 8%, 9%, 10%, 11%, 12% 13%, 14%, 15%, 16,%, 17%, 18%, 19%, 20%, 25%, 30%, 35%, 40%, 45%, 50%, 60%, 70%, 80%, or 90% native royalactin, including ranges between any two of the listed values, for example 1%-90%, 1%-50%, 1%-30%, 1%-20%, 1%-10%, 5%-90%, 5%-50%, 5%-30%, 5%-20%, 5%-10%, 10%-90%, 10%-50%, 10%-30%, 10%-20%, 20%-90%, 20%-50%, or 20%-30%. In some embodiments, the antibody comprises a mouse antibody. In some embodiments, the antibody of any method for purifying native royalactin as described herein comprises a heavy chain variable region (HCVR) comprising: a CDR3 domain of the CDR3 domain of SEQ NO: 6; a CDR2 domain of the CDR2 domain of SEQ NO: 6; and a CDR1 domain of the CDR1 domain of SEQ NO: 6; and a light chain variable region (LCVR) comprising: a CDR3 domain of the CDR3 domain of SEQ NO: 8; a CDR2 domain of the CDR2 domain of SEQ NO: 8; and a CDR1 domain of the CDR1 domain of SEQ NO: 8. In some embodiments, the antibody of any method for purifying native royalactin as described herein comprises a HCVR of the HCVR of SEQ ID NO: 6; and a LCVR of the LCVR of SEQ ID NO: 8. In some embodiments, the antibody comprises antibody 4G6C5, antibody 8C5C9, antibody 8C5D3, antibody 4G6E2, or antibody 9G6A2, or a binding fragment thereof. In some embodiments, the antibody comprises (a) a heavy chain variable region (HCVR) having a CDR3 domain of the CDR3 domain of antibody 4G6C5, a CDR2 domain of the CDR2 domain of antibody 4G6C5, and a CDR1 domain of the CDR1 domain of antibody 4G6C5, and a light chain variable region (LCVR) having a CDR3 domain of the CDR3 domain of antibody 4G6C5, a CDR2 domain of the CDR2 domain of antibody 4G6C5, and a CDR1 domain of the CDR1 domain of antibody 4G6C5; or (b) a HCVR having a CDR3 domain of the CDR3 domain of antibody 8C5C9, a CDR2 domain of the CDR2 domain of antibody 8C5C9, and a CDR1 domain of the CDR1 domain of antibody 8C5C9, and a LCVR having a CDR3 domain of the CDR3 domain of antibody 8C5C9, a CDR2 domain of the CDR2 domain of antibody 8C5C9, and a CDR1 domain of the CDR1 domain of antibody 8C5C9; or (c) a HCVR having a CDR3 domain of the CDR3 domain of antibody 8C5D3, a CDR2 domain of the CDR2 domain of antibody 8C5D3, and a CDR1 domain of the CDR1 domain of antibody 8C5D3, and a LCVR having a CDR3 domain of the CDR3 domain of antibody 8C5D3, a CDR2 domain of the CDR2 domain of antibody 8C5D3, and a CDR1 domain of the CDR1 domain of antibody 8C5D3; or (d) a HCVR having a CDR3 domain of the CDR3 domain of antibody 4G6E2, a CDR2 domain of the CDR2 domain of antibody 4G6E2, and a CDR1 domain of the CDR1 domain of antibody 4G6E2, and a LCVR having a CDR3 domain of the CDR3 domain of antibody 4G6E2, a CDR2 domain of the CDR2 domain of antibody 4G6E2, and a CDR1 domain of the CDR1 domain of antibody 4G6E2; or (e) a HCVR having a CDR3 domain of the CDR3 domain of antibody 9G6A2, a CDR2 domain of the CDR2 domain of antibody 9G6A2, and a CDR1 domain of the CDR1 domain of antibody 9G6A2, and a LCVR having a CDR3 domain of the CDR3 domain of antibody 9G6A2, a CDR2 domain of the CDR2 domain of antibody 9G6A2, and a CDR1 domain of the CDR1 domain of antibody 9G6A2. In some embodiments, the antibody competes for binding to royalactin with at least one of the antibodies listed above. In some embodiments, the biological matter comprises insect royal jelly. In some embodiments, the biological matter comprises extracts of cells genetically engineered to produce native royalactin. In some embodiments, the insect is of the genus *Apis*. In some embodiments, the substrate comprises agarose. In some embodiments, separating, and removing comprise immunoprecipitation. In some embodiments, said contacting, separating, and removing are performed using an affinity column. In some embodiments, the composition comprising purified native royalactin (and enriched for native royalactin) comprises at least 30% (w/w) lyophilized native royalactin. In some embodiments, the topical cosmetic product comprising the native royalactin comprises a topical lotion, cream, paste, gel, spray, powder, or pencil. In some embodiments, topical cosmetic product comprises at least 10% royalactin (w/w). In some embodiments, a kit comprising the composition comprising purified native royalactin, as described herein, is provided. As such, in some embodiments, a kit comprises a composition enriched for native royalactin as described herein Some aspects include an isolated monoclonal antibody that binds specifically to royalactin. In some embodiments, the antibody comprises antibody 4G6C5, antibody 8C5C9, antibody 8C5D3, antibody 4G6E2, or antibody 9G6A2, or the LCVR and HCDR's of one of these antibodies, or the HCDR1, HCDR2, HDCR3, LCDR1, LCDR2, and LCDR3 of one of these antibodies. In some embodiments, the isolated monoclonal antibody competes for binding to royalactin with one of the antibodies listed above. In some embodiments, the antibody comprises a mouse antibody. Some aspects include a kit comprising the antibody specific for royalactin. In some embodiments, the isolated monoclonal antibody comprises a heavy chain variable region (HCVR) comprising: a CDR3 domain of the CDR3 domain of SEQ NO: 6; a CDR2 domain of the CDR2 domain of SEQ NO: 6; and a CDR1 domain of the CDR1 domain of SEQ NO: 6; and a light chain variable region (LCVR) comprising: a CDR3 domain of the CDR3 domain of SEQ NO: 8; a CDR2 domain of the CDR2 domain of SEQ NO: 8; and a CDR1 domain of the CDR1 domain of SEQ NO: 8. In some embodiments, the isolated monoclonal antibody comprises a HCVR of the HCVR of SEQ ID NO: 6; and a LCVR of the LCVR of SEQ ID NO: 8.

Some aspects include an isolated nucleic acid that comprises, consists essentially of, or consists of a nucleic acid sequence encoding an isolated monoclonal antibody that binds specifically to royalactin. In some embodiments, the isolated monoclonal antibody comprises a (HCVR) comprising: a CDR3 domain of the CDR3 domain of SEQ NO: 6; a CDR2 domain of the CDR2 domain of SEQ NO: 6; and a CDR1 domain of the CDR1 domain of SEQ NO: 6; and a light chain variable region (LCVR) comprising: a CDR3 domain of the CDR3 domain of SEQ NO: 8; a CDR2 domain of the CDR2 domain of SEQ NO: 8; and a CDR1 domain of the CDR1 domain of SEQ NO: 8. In some embodiments, the isolated nucleic acid encodes an antibody that binds specifically to a royalactin comprising, consisting essentially of, or consisting of SEQ ID NO: 2. In some embodiments, the nucleic acid encoding the HCVR and the nucleic acid encoding the LCVR are comprised by the same polynucleotide. In some embodiments, the nucleic acid encoding the HCVR and the nucleic acid encoding the LCVR are comprised by different polynucleotides (for example, separate vectors, or separate chromosomes). In some embodiments, the nucleic acid comprises, consists essentially of, or consists of a nucleic acid of SEQ ID NO: 5 and a nucleic acid of SEQ ID NO: 7. The nucleic acid of SEQ ID NO: 5 can encode a heavy chain variable region, and the nucleic acid of SEQ ID NO: 7 can encode a light chain variable region. In some embodiments, the nucleic acid of SEQ ID NO: 5 and the nucleic acid of SEQ ID NO: 7 are comprised by the same nucleic acid molecule, for example a single vector, and under the control of separate promoters, or under the control of a single promoter and separated by an IRES or a 2A sequence. In some embodiments, the nucleic acid of SEQ ID NO: 5 and the nucleic acid of SEQ ID NO: 7 are comprised by different nucleic acid molecules. In some embodiments, the nucleic acid of SEQ ID NO: 5 and the nucleic acid of SEQ ID NO: 7 are comprised by different nucleic acid molecules that are in the same composition. In some embodiments, the isolated nucleic acid encodes an isolated monoclonal antibody that binds specifically to royalactin comprising, consisting essentially of, or consisting of the polypeptide of SEQ ID NO: 2. In some embodiments, a hybridoma cell for expressing an isolated monoclonal antibody that binds specifically to royalactin comprises a nucleic acid of SEQ ID NO: 5 and a nucleic acid of SEQ ID NO: 7.

BRIEF DESCRIPTION OF THE DRAWINGS

FIG. 1A is a diagram of the nucleotide sequence encoding honeybee royalactin (SEQ ID NO: 1)(GenBank: AF000633.1). FIG. 1B is a diagram of the amino acid sequence of royalactin (SEQ ID NO: 2).

FIG. 2A is a diagram of the nucleotide sequence encoding royalactin fusion protein (SEQ ID NO: 3), which can be used to generate antibodies specific for royalactin in some embodiments. FIG. 2B a diagram of the amino acid sequence of the royalactin fusion protein (SEQ ID NO: 4). Specific elements of the fusion protein including area of shared identity with the native protein, FLAG tag, and poly-His tag are noted.

FIGS. 3A and 3B are images of dot immunoblot assays measuring affinity of monoclonal antibodies specific for RA in accordance with some embodiments herein.

FIG. 4A shows the results of immunoprecipitation of 500 ng RA starting material using monoclonal antibodies 19 and 20. FIG. 4B shows the results of immunoprecipitation of 500 ng RA starting material using monoclonal antibodies 21, 22, and 23.

FIG. 5A is an image of a Coomasie-stained SDS-PAGE gel of immunoprecipitation of native royalactin from royal jelly using a monoclonal antibody that binds to royalactin in accordance with some embodiments herein.

FIGS. 6A-D are a series of diagrams illustrating sequences of heavy chain variable regions and light chain variable regions of antibody 4G6C5 of some embodiments. FIG. 6A illustrates a nucleic acid (SEQ ID NO: 5) encoding a heavy chain variable region of antibody 4G6C5 of some embodiments. FIG. 6B illustrates a polypeptide (SEQ ID NO: 6) comprising a heavy chain variable region of antibody 4G6C5 of some embodiments. FIG. 6C illustrates a nucleic acid (SEQ ID NO: 7) encoding a light chain variable region of antibody 4G6C5 of some embodiments. FIG. 6D illustrates a polypeptide (SEQ ID NO: 8) comprising a light chain variable region of antibody 4G6C5 of some embodiments.

DETAILED DESCRIPTION

Figure 3B:
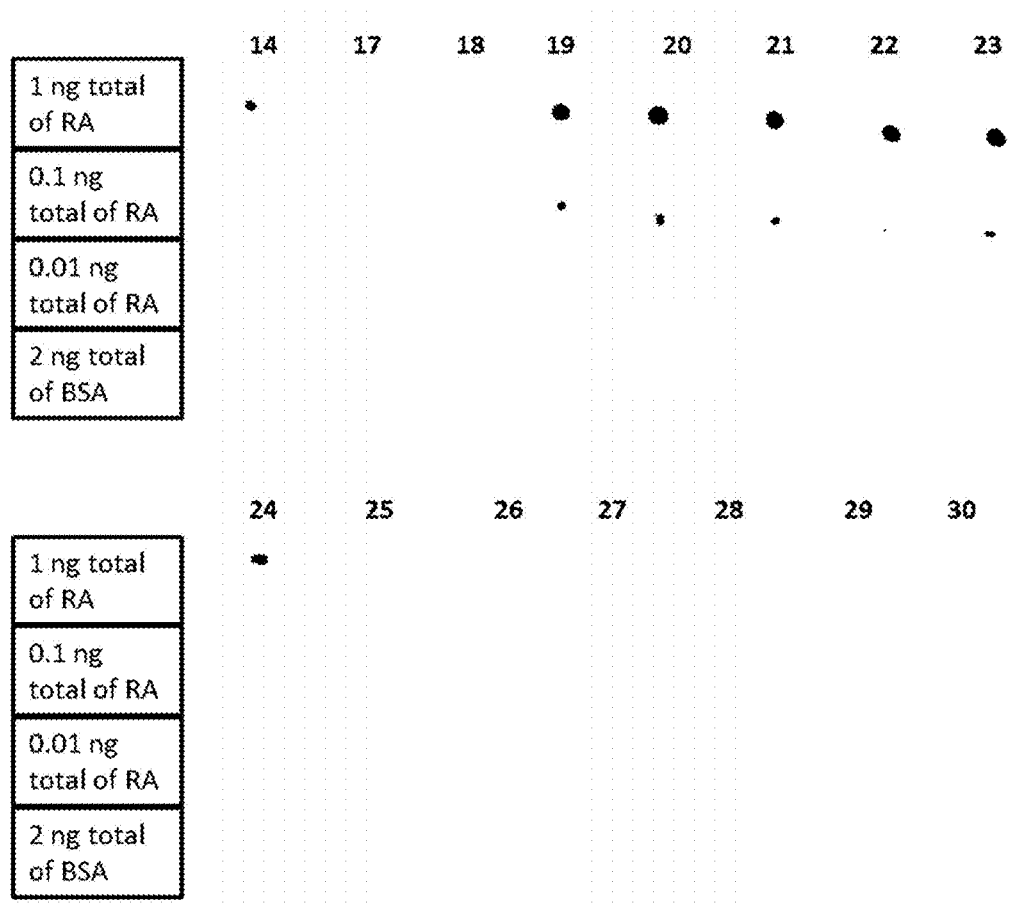

Described herein are methods and compositions for purifying royalactin (RA) protein, and compositions comprising purified royalactin. In some embodiments, royalactin is purified using antibodies specific for royalactin, for example monoclonal antibodies as described herein, which bind to native royalactin, so as to produce a composition comprising purified native royalactin. Biological matter comprising native royalactin can be solubilized in aqueous solution, and contacted with an antibody specific for royalactin. In some embodiments, royalactin is purified in its native conformation, thus producing a composition comprising purified royalactin in its native conformation. In some embodiments, methods of making compositions comprising purified native royalactin are described. In some embodiments, one or more monoclonal antibodies specific for royalactin, and which bind to native royalactin, are provided.

Female honeybee larva can develop into either workers or queens. Royal jelly is a substance secreted by worker bees. Royal jelly is a complex mix of various vitamins, carbohydrates, fatty acids, and proteins. Only female larvae fed royal jelly will develop into queens. Royalactin (for example, as set forth in SEQ ID NO: 2) is a monomeric 57 kDa protein without known family members (i.e., paralogs), that is a component of royal jelly. It has been shown that royalactin by itself is capable of inducing female larvae to differentiate into queens. Royalactin replicates the effects of royal jelly with increased growth rates and increased longevity. Royalactin has also been found to have the same effect of increased growth and longevity in another insect, *Drosophila melanogaster*, or the common fruit fly. Royalactin has also been found to have the effect of prolonging longevity in the non-insect nematode, Caenorhabditis *elegans*. In both insects and worms, royalactin has been found to act primarily through members of the epidermal growth factor receptors (EGFRs). This has been demonstrated in both *Drosophila* and *C. elegans* through the use of knockout mutants. Finally, royalactin has also been demonstrated to have mitogenic effects on mammalian cells. In view of high degrees of conservation of royalactin among honeybees, it is contemplated that royalactin of the genus of honeybees, or, more precisely, royalactin of insects of the genus *Apis*, has biological activities as described herein (such as mitogenic activities on mammalian cells and activity in would healing), and can be purified using antibodies and methods described herein. Accordingly, as used herein "royalactin" refers royalactin of the genus *Apis*. Such royalactin can be found in royal jelly of insects of the genus *Apis*. In some embodiments, royalactin comprises or consists of a protein having the amino acid sequence of SEQ ID NO: 2. In some embodiments, royalactin is encoded by the nucleic acid of SEQ ID NO: 1. In some embodiments, royalactin comprises a royalactin of the genus *Apis*. In some embodiments, royalactin comprises a royalactin of *Apis mellifera*. In some embodiments, the royalactin of the genus *Apis* further comprises an affinity tag, for example a his-, FLAG, and/or HA-tag.

It is contemplated that royalactin in its native confirmation possesses the biological activities noted herein, but that other proteins comprising the polypeptide sequence of royalactin (for example, denatured royalactin, or synthetic royalactin polypeptides or fragments) do not necessarily possess these activities, or possess less potent activities. Accordingly, in some embodiments, an antibody that bind specifically to royalactin is provided. The antibody specific for royalactin can bind to native royalactin. As used herein "native" royalactin refers to a non-denatured royalactin protein of the genus *Apis*, as can be found in royal jelly, for example, a protein of SEQ ID NO: 2. The antibody can be used to purify native royalactin, so as to produce compositions comprising purified native royalactin as described herein.

Antibodies

Antibodies are members of the class of immunoglobulin molecules. Full-length antibodies are heterotetrameric glycoprotein that have a molecular weight of about 150 kDa. See Janeway et al. Immunobiology 5th ed., New York: Garland Science 2001, which is hereby incorporated by reference in its entirety. The typical antibody comprises two light chains, each comprising a variable light (VL) domain and a light chain constant region, and two heavy chains, which each comprise a variable heavy (VH) domain and a heavy chain constant region. The chains of the antibody are bonded together via disulfide bonds. From N- to C-terminus, each heavy chain variable region comprises a heavy chain variable region comprising: a first heavy framework region (HFR1), a first heavy complementarity determining region (HCDR1), a second heavy framework region (HFR2), a second heavy complementarity determining region (HCDR2), a third heavy framework region (HFR3), a third heavy complementarity determining region (HCDR3), and a fourth heavy framework region (HFR4). Downstream (toward the direction the C-terminus) of the heavy chain variable region is the heavy chain constant region, which includes, (from N- to C-terminus) the constant heavy 1 (CH1), constant heavy 2 (CH2) and constant heavy 3 (CH3) domains. In human antibodies, the heavy chain constant region may be an IgG1, IgG2, IgG3, or IgG4 type. From N- to C-terminus, each light chain comprises a light chain variable region comprising: a first light framework region (LFR1), a first light complementarity determining region (LCDR1), a second light framework region (LFR2), a second light complementarity determining region (LCDR2), a third light framework region (LFR3), a third light complementarity determining region (LCDR3), and a fourth light framework region (LFR4). Downstream (toward the direction the C-terminus) of the light chain variable region is the light chain constant region. In human antibodies, the light chain constant region may be either a kappa or lambda type. The CDR's represent hypervariable loops, and the six CDR's, or subsets thereof are involved in epitope recognition and binding by the antibody. The CDR's can be numbered according to any art-recognized definition, for example the definition of Kabat (See Kabat et al., Sequences of Proteins of Immunological Interest, 5th Ed. Public Health Service, National Institutes of Health, Bethesda, Md. (1991)), the definition of Chothia (See Chothia and Lesk, J. Mol. Biol. 196:901-917 (1987)), and the AbM definition (Martin et al., Proc. Natl. Acad. Sci. USA, 86:9268-9272 (1989)), each of which is hereby incorporated by reference in its entirety. In some embodiments, the CDRs are defined according to the group selected from the definition of Kabat, the definition of Chothia, the AbM definition, the contact definition, and the IMGT definition. As used herein, the term "antibody" encompasses full-length monoclonal and polyclonal antibodies, as well as function binding fragments thereof, such as Fab, Fab' F(ab')2, Fv, diabodies, and the like. In some embodiments, the antibody against royalactin is a full length antibody. An antibody will be understood to "specifically bind" (or "bind specifically" to, or be "specific for," including variations of these root terms) if, in a heterogeneous population of proteins, macromolecules, or other possible binding targets of antibodies, the binding of the antibody is determinative of the presence of the particular antigen. Thus, an antibody that is specific to royalactin will be understood to bind to a substance comprising royalactin at a level higher than background, and will be understood to bind to royalactin preferably, without substantially binding to other potential antigens in a substance. It is noted that an antibody specific for royalactin can bind to native royalactin, and may also bind to other forms of royalactin, but the binding activity to native royalactin will be useful for purifying native royalactin.

Monoclonal antibodies in accordance with some embodiments herein can be constructed by exposing a host organism to one or more administrations of an antigen comprising royalactin. The antigen comprising royalactin further comprises a carrier protein such as keyhole limpet hemocyanin (KLH). A variety of hosts are suitable in accordance with some embodiments, herein, for example mouse, rat, rabbit, guinea pig, hamster, donkey, goat, horse, and the like. Accordingly, it is understood that in some embodiments, antibodies of any of a desired host type can be produced. In some embodiments, the host comprises a non-human mammal. In some embodiments, the host is a rodent such as a mouse or a rat. Antibody-producing cells, typically B cells, can be isolated from the host. In some embodiments, an initial administration of antigen comprising royalactin to a host is followed by one or more subsequent boosts. In some embodiments, hybridomas are constructed from antibody-producing cells, and hybridomas are screened for production of antibodies with desired characteristics, such as affinity for native royalactin. In some embodiments, a phage display library comprising nucleic acids encoding antibodies or binding fragments thereof is produced (See Clackson and Wells, Trends Biotech. 12: 173-184 (1994)). The phage display library can be screened for antibodies or binding fragments with affinity to the desired target, for example native royalactin. Accordingly, a phage display library can be used for initial screens for antibodies with suitable affinity, and can also be used to screen for variants with suitable affinity to native royalactin, for example to screen for higher affinity variants of a lead monoclonal antibody. In some embodiments, a phage display library is screened to identify nucleic acids that encode an antibody with suitable binding characteristics to native royalactin. In some embodiments, a phage display library is used to screen for high-affinity variants of a monoclonal antibody that binds to native royalactin. The phage display library can be screened against an aqueous solution comprising solubilized native royalactin, for example native royalactin. Techniques for generating monoclonal antibodies are discussed, for example, in Greenfield (2014), Antibodies: A Laboratory Manual, Second Edition, Cold Spring Harbor Laboratory Press, New York, which is hereby incorporated by reference in its entirety.

In some embodiments, two or more monoclonal antibodies compete for binding to an epitope on royalactin, for example native royalactin. As used herein, two antibodies "compete" for binding to royalactin when a first antibody inhibits binding of a second antibody to a common epitope of royalactin. Competition can be ascertained using a number of suitable assays, for example competition ELISA, or competition radioimmunoassays. For example, binding of a labeled first antibody specific for royalactin can be determined in the presence and absence of an unlabeled (or differently labeled) second antibody specific for royalactin to determine if binding of the labeled first antibody is reduced in the presence of the second antibody. The first antibody can be labeled directly or indirectly. Some epitopes can be linear epitopes, which represent a particular set of residues on royalactin, and can be confirmed, for example, by mapping of antibody binding to royalactin peptides and/or deletion peptides. For example, a linear epitope of royalactin in accordance with some embodiments can comprise an epitope in residues 1-10, 11-20, 21-30, 31-40, 41-50, 51-60, 61-70, 71-80, 81-90, 91-100, 101-110, 111-120, 121-130, 131-140, 141-150, 151-160, 161-170, 171-180, 181-190, 191-200, 201-210, 211-220, 221-230, 231-240, 241-250, 251-260, 261-270, 271-280, 281-290, 291-300, 301-310, 311-320, 321-330, 331-340, 341-350, 351-360, 361-370, 371-380, 381-390, 391-400, 401-410, 411-420, or 421-432 of SEQ ID NO: 2. Some epitopes can be conformational, and as such can be present on native royalactin as a result of its three-dimensional structure, but do not necessarily comprise consecutive resides in the primary amino acid sequence of royalactin. As such, in some embodiments, a monoclonal antibody specific for royalactin as described herein specifically binds to a conformational epitope on native royalactin, but binds with lower affinity, or does not appreciably bind to denatured royalactin. In some embodiments, a monoclonal antibody specific for royalactin as described herein specifically binds to a linear epitope on royalactin. In some embodiments, an antibody competes for binding to royalactin with at least one of antibody 4G6C5, antibody 8C5C9, antibody 8C5D3, antibody 4G6E2, or antibody 9G6A2, or an antibody comprising the six CDR's (HCDR1, HCDR2, HCDR3, LCDR1, LCDR2, LCDR3) of any of the listed antibodies. In some embodiments, an antibody against royalactin competes for binding to royalactin with two or more of antibody 4G6C5, antibody 8C5C9, antibody 8C5D3, antibody 4G6E2, or antibody 9G6A2. The HCVR and LCVR sequences of antibody 4G6C5 are shown in FIGS. 6B and 6D, respectively. Nucleic acids encoding the noted HCVR and LCVR are shown if FIGS. 6A and 6C, respectively. It will be appreciated that wherever antibody "4G6C5" is mentioned herein (or variations of this root term, such as "mAb 4G6C5," "clone 4G6C5" and the like), an antibody comprising a HCVR comprising: a CDR3 domain of the CDR3 domain of SEQ NO: 6; a CDR2 domain of the CDR2 domain of SEQ NO: 6; and a CDR1 domain of the CDR1 domain of SEQ NO: 6; and a LCVR comprising: a CDR3 domain of the CDR3 domain of SEQ NO: 8; a CDR2 domain of the CDR2 domain of SEQ NO: 8; and a CDR1 domain of the CDR1 domain of SEQ NO: 8 is expressly contemplated. It will be appreciated that wherever antibody "4G6C5" (or variations of this root term) is mentioned herein, an antibody comprising a HCVR that is an HCVR in of SEQ NO: 6; and a LCVR that is an LCVR is SEQ NO: 8 is also expressly contemplated.

In some embodiments, an isolated monoclonal antibody (which can be used as an antibody of any method for purifying native royalactin as described herein) comprises a heavy chain variable region (HCVR) comprising: a CDR3 domain of the CDR3 domain of SEQ NO: 6; a CDR2 domain of the CDR2 domain of SEQ NO: 6; and a CDR1 domain of the CDR1 domain of SEQ NO: 6; and a light chain variable region (LCVR) comprising: a CDR3 domain of the CDR3 domain of SEQ NO: 8; a CDR2 domain of the CDR2 domain of SEQ NO: 8; and a CDR1 domain of the CDR1 domain of SEQ NO: 8. In some embodiments, the isolated monoclonal antibody (which can be used as an antibody of any method for purifying native royalactin as described herein) comprises a heavy chain variable region (HCVR) comprising: a CDR3 domain of the CDR3 domain of SEQ NO: 6; a CDR2 domain of the CDR2 domain of SEQ NO: 6; and a CDR1 domain of the CDR1 domain of SEQ NO: 6; and a light chain variable region (LCVR) comprising: a CDR3 domain of the CDR3 domain of SEQ NO: 8; a CDR2 domain of the CDR2 domain of SEQ NO: 8; and a CDR1 domain of the CDR1 domain of SEQ NO: 8, and the HCVR comprises a polypeptide at least 85% identical to SEQ ID NO: 6, and the LCVR comprises a polypeptide at least 85% identical to SEQ ID NO: 8. For example, the HCVR can comprise a polypeptide at least 90% identical to SEQ ID NO: 6, and the LCVR can comprise a polypeptide at least 90% identical to SEQ ID NO: 8. For example, the HCVR can comprise a polypeptide at least 95% identical to SEQ ID NO: 6, and the LCVR can comprise a polypeptide at least 95% identical to SEQ ID NO: 8. For example, the HCVR can comprise a polypeptide at least 97% identical to SEQ ID NO: 6, and the LCVR can comprise a polypeptide at least 97% identical to SEQ ID NO: 8. For example, the HCVR can comprise a polypeptide at least 99% identical to SEQ ID NO: 6, and the LCVR can comprise a polypeptide at least 99% identical to SEQ ID NO: 8. In some embodiments, the isolated monoclonal antibody (which can be used as an antibody of any method for purifying native royalactin as described herein) comprises a HCVR of the HCVR of SEQ ID NO: 6; and a LCVR of the LCVR of SEQ ID NO: 8.

Some embodiments include a nucleic acid that encodes an isolated monoclonal antibody that binds specifically to royalactin. In some embodiments, the nucleic acid can encode an antibody comprising a heavy chain variable region (HCVR) comprising: a CDR3 domain of the CDR3 domain of SEQ NO: 6; a CDR2 domain of the CDR2 domain of SEQ NO: 6; and a CDR1 domain of the CDR1 domain of SEQ NO: 6; and a light chain variable region (LCVR) comprising: a CDR3 domain of the CDR3 domain of SEQ NO: 8; a CDR2 domain of the CDR2 domain of SEQ NO: 8; and a CDR1 domain of the CDR1 domain of SEQ NO: 8. In some embodiments, the nucleic acid comprises, consists essentially of, or consists of the nucleic acid sequence of SEQ ID NO: 5 and the nucleic acid sequence of SEQ ID NO: 7. The nucleic acid of SEQ ID NO: 5 can encode a HCVR of an antibody that binds specifically to royalactin, and the nucleic acid of SEQ ID NO: 7 can encode a LCVR of an antibody that binds specifically to royalactin. In some embodiments, the nucleic acid of SEQ ID NO: 5 and the nucleic acid of SEQ ID NO: 7 are part of the same polynucleotide (for example, are on the same vector or the same chromosome). In some embodiments, the nucleic acid of SEQ ID NO: 5 and the nucleic acid of SEQ ID NO: 7 are parts of different polynucleotides (for example, on different vectors or different chromosome).

In some embodiments, polyclonal antibodies to native royalactin are provided. Polyclonal antibodies do not necessarily bind to the same epitope on native royalactin, and thus, do not necessarily compete with each other for binding. Polyclonal antibodies (which may also be referred to as "antisera") can be obtained by immunizing a host with an antigen comprising royalactin as described herein Immune sera from the host can be obtained, and polyclonal antibodies with affinity to royalactin can be obtained through affinity purification, for example affinity chromatography or immunoprecipitation. For example, royalactin such as royalactin in a native conformation can be immobilized on a solid phase and contacted with polyclonal serum, so that polyclonal antibodies, specific for royalactin bind to the native royalactin immobilized on the solid phase. The solid phase can then be washed to remove antibodies not specific for royalactin and any undesired substances. Then, antibodies specific for royalactin can be recovered from the solid phase, for example by elution.

Methods of Purifying Royalactin

Some embodiments include methods for purifying royalactin. It is noted that as used herein, "purifying" a desired substance such as native royalactin refers to separating that substance from other substances in a heterogeneous composition, for example by removing and retaining the desired substance from the heterogeneous composition, and/or by appreciably removing the other substances from the heterogeneous composition. As such, "purified" royalactin (including variations of this root term) need not consist entirely of royalactin, but also encompasses compositions in which royalactin is appreciably enriched compared to a starting heterogeneous composition. Accordingly, methods of purifying royalactin as discussed in accordance with some embodiments herein will be understood to produce compositions enriched for royalactin, for examples comprising, consisting essentially of, or consisting of royalactin, such as native royalactin. Products that such compositions in which royalactin is appreciable enriched are also understood to comprise purified royalactin. For similar reasons, a crude biological extract (comprising royalactin and other substances) would be understood not to comprise "purified" royalactin as used herein. The method can comprise solubilizing biological matter comprising native royalactin can in an aqueous solution. The method can comprise contacting the aqueous solution comprising the solubilized biological matter with an antibody immobilized on a substrate, in which the monoclonal antibody binds specifically to royalactin. The antibody can bind to native royalactin. The method can comprise separating native royalactin bound to the antibodies from the aqueous solution (e.g., by removing the aqueous solution, by washing the antibodies and substrate, and/or by removing the substrate from the aqueous solution). The bound native royalactin can then be removed from the substrate, for example by elution. The native royalactin thus obtained represents a composition comprising purified native royalactin. In some embodiments, the composition comprising purified royalactin comprises at least 1% (w/w) native royalactin, for example, at least 1%, 2%, 3%, 4%, 5%, 6%, 7%, 8%, 9%, 10%, 11%, 12% 13%, 14%, 15%, 16,%, 17%, 18%, 19%, 20%, 25%, 30%, 35%, 40%, 45%, 50%, 60%, 70%, 80%, or 90% native royalactin, including ranges between any two of the listed values, for example 1%-90%, 1%-50%, 1%-30%, 1%-20%, 1%-10%, 5%-90%, 5%-50%, 5%-30%, 5%-20%, 5%-10%, 10%-90%, 10%-50%, 10%-30%, 10%-20%, 20%-90%, 20%-50%, or 20%-30%. In some embodiments, the purified royalactin undergoes further purification, for example filtration, centrifugation, size exclusion chromatography, or one or more additional rounds of affinity purification using an antibody specific for royalactin. In some embodiments, the purified native royalactin is used to produce a cosmetic product comprising native royalactin as described herein. In some embodiments, the purified native royalactin is comprised in a kit for producing a cosmetic product as described herein. Furthermore, it will be understood that wherever a method for purifying royalactin is disclosed herein and the method comprises an antibody, an antibody for use in purifying royalactin is also expressly contemplated.

In some embodiments, antibodies directed to royalactin can be used to enrich for or purify native royalactin by immobilizing the antibodies on a substrate, binding native royalactin in aqueous solution to the antibodies, separating the bound royalactin from the remaining aqueous solution (e.g. by washing and/or physically separating the substrate from the aqueous solution), and eluting (or otherwise removing) the bound native royalactin. In some embodiments, the antibodies comprise, consist essentially of, or consist of an antibody comprising a CDR3 domain of the CDR3 domain of SEQ NO: 6; a CDR2 domain of the CDR2 domain of SEQ NO: 6; and a CDR1 domain of the CDR1 domain of SEQ NO: 6; and a light chain variable region (LCVR) comprising: a CDR3 domain of the CDR3 domain of SEQ NO: 8; a CDR2 domain of the CDR2 domain of SEQ NO: 8; and a CDR1 domain of the CDR1 domain of SEQ NO: 8. In some embodiments, the antibodies comprise, consist essentially of, or consist of an antibody comprising comprises a HCVR of the HCVR of SEQ ID NO: 6; and a LCVR of the LCVR of SEQ ID NO: 8. In some embodiments, the antibodies comprise one or more of antibody 4G6C5, antibody 8C5C9, antibody 8C5D3, antibody 4G6E2, or antibody 9G6A2. In some embodiments, the antibodies compete for binding to royalactin with one or more of antibody 4G6C5, antibody 8C5C9, antibody 8C5D3, antibody 4G6E2, or antibody 9G6A2. A number of suitable techniques can be used to immobilize antibodies on a substrate in accordance with some embodiments herein. For example, antibodies can be immobilized on a substrate though covalent coupling with activated beads (examples include Affi-gel 10, Biorad Laboratories, Richmond, Calif.) or by contacting the antibodies with beads that are already coupled to proteins, like Protein A, with high affinity for IgG (examples include Pierce Protein A Plus Agarose, ThermoFisher Scientific, Waltham, Mass.). In some embodiments, the antibodies specific for royalactin are used to purify native royalactin via immunoprecipitation. In some embodiments, the antibodies specific for royalactin are used to purify native royalactin via affinity chromatography. In some embodiments, after native royalactin is bound to antibodies on the substrate, one or more washes are performed, so as to separate the substrate and antibodies from the initial solution that had comprised the royalactin, prior to eluting or otherwise removing the bound native royalactin.

In some embodiments, the antibodies specific for royalactin are immobilized on a substrate directly, for example by covalent linkage such as cross-linking. In some embodiments, the antibodies specific for royalactin are immobilized on a substrate indirectly, for example by contacting the antibodies specific for royalactin with a secondary antibody immobilized on the substrate, in which the secondary antibody is specific for the host of the antibodies specific for royalactin.

In some embodiments, royalactin comprising an affinity tag, for example a his- or a FLAG, or a hemagglutinin (HA) tag, is affinity purified. Such affinity-tagged royalactin proteins can be produced in cell cultures, for example insect or bacterial cells comprising a nucleic acid encoding the affinity-tagged royalactin. The royalactin can be contacted with a solid phase with affinity for the affinity tag. For example, heavy metal ions such as Ni or Co in a solid phase can have affinity for a his-tag. For example, antibodies immobilized on a solid phase can have affinity for a FLAG or HA tag. By way of example, a royalactin protein comprising a his- and FLAG-tag is shown in SEQ ID NO: 4. As shown in Example 1, this affinity-tagged royalactin protein was affinity purified and shown to have biological activity.

In some embodiments, the substrate comprises a bead that is paramagnetic to aid in the process of enrichment or purification (examples include Dynabeads Protein A Magnetic Beads, ThermoFisher Scientific, Waltham, Mass.). The process is similar to the batch purification approach noted above with the exception that the beads are collected using a magnet instead of centrifugation. In some embodiments, the substrate comprises agarose, for example an agarose bead or an agarose resin.

In some embodiments, a crude solution of biological material comprising royalactin (e.g., royal jelly, cell cultures, or cell culture extracts), is contacted with the antibodies specific for royalactin. In some embodiments, the solution is an aqueous solution. In some embodiments, the biological material comprising royalactin comprises, consists of, or consists essentially of royal jelly. In some embodiments, the biological material comprising royalactin comprises, consists of, or consists essentially of cell cultures or extracts thereof, for example cultures of transgenic cells that express royalactin. In some embodiments, the cells comprise bacterial cells or insect cells. In some embodiments, a solution of biological material comprising native royalactin undergoes one or more initial purification steps before being contacted with the antibodies specific for royalactin. For example, in some embodiments, the solution of biological material comprising royalactin can undergo initial rounds of filtration, centrifugation, size exclusion chromatography, or the like to enrich it for royalactin, and/or to remove undesired substances. The solution that undergoes initial purification can then be subject to further methods of purification of royalactin using antibodies against royalactin as described herein.

In some embodiments, the antibodies specific for royalactin immobilized on substrates (e.g., beads) are placed in a column and the solution containing biological matter containing native royalactin is passed through the column. After several washes, the native royalactin is eluted using a specific buffer that dissociated the antigen from the antibody, and collected in the flowthrough from the column. Purified native royalactin can thus be obtained, yielding a composition comprising purified native royalactin. In some embodiments, the purification can be done in a batch method. Instead of using a column, the beads are added to the crude solution. Centrifugation can be used to pellet the beads, and they are washed using the same approach. The final elution can also be the same as with the column with the exception that the final eluent is aspirated off the beads after they have been centrifuged down. Purified native royalactin can thus be obtained, yielding a composition comprising purified native royalactin.

Compositions Comprising Purified Native Royalactin

In some embodiments, methods of purifying royalactin as described herein produce compositions enriched for, consisting or, or consisting essentially of purified native royalactin. In some embodiments, the composition comprises native royalactin in a solvent, such as an aqueous solution. In some embodiments, the composition comprises purified native royalactin in a dry form, such a lyophilized or spray-dried. It is contemplated that compositions comprising purified native royalactin can be useful for "cosmetic products" (which may also be referred to herein as "cosmetic compositions," including variations of either root term). In some embodiments, the cosmetic product comprises a topical cosmetic product such as a topical lotion, cream, paste, gel, spray, powder, pencil, and the like. Accordingly, in some embodiments, a cosmetic product comprises purified native royalactin as described herein. In some embodiments, the composition comprising purified native royalactin is used to make a cosmetic product comprising native royalactin. In some embodiments, the composition comprising purified native royalactin is produced using a purification method as described herein, and then used to make a cosmetic product comprising native royalactin without an intervening step. In some embodiments, the composition comprising purified native royalactin is dried, for example by lyophilization or spray-drying, and can be subsequently used to make a cosmetic product comprising native royalactin. In some embodiments, the composition comprising purified native royalactin is included in a kit for making a cosmetic product comprising native royalactin. In some embodiments, the kit further comprises instructions directing a user on how the composition comprising purified native royalactin can be incorporated into a cosmetic product. In some embodiments, the kit further comprises instructions directing a user on how to reconstitute the composition comprising purified native royalactin. In some embodiments, the composition comprising purified native royalactin comprises at least 1% (w/w) native royalactin, for example, at least 1%, 2%, 3%, 4%, 5%, 6%, 7%, 8%, 9%, 10%, 11%, 12% 13%, 14%, 15%, 16,%, 17%, 18%, 19%, 20%, 25%, 30%, 35%, 40%, 45%, 50%, 60%, 70%, 80%, or 90% native royalactin, including ranges between any two of the listed values, for example 1%-90%, 1%-50%, 1%-30%, 1%-20%, 1%-10%, 5%-90%, 5%-50%, 5%-30%, 5%-20%, 5%-10%, 10%-90%, 10%-50%, 10%-30%, 10%-20%, 20%-90%, 20%-50%, or 20%-30%.

In some embodiments, the cosmetic product comprising native royalactin comprises at least 1% (w/w) native royalactin, for example, at least 1%, 2%, 3%, 4%, 5%, 6%, 7%, 8%, 9%, 10%, 11%, 12% 13%, 14%, 15%, 16,%, 17%, 18%, 19%, 20%, 25%, 30%, 35%, 40%, 45%, 50%, 60%, 70%, or 80% royalactin, including ranges between any two of the listed values, for example 1%-80%, 1%-50%, 1%-30%, 1%-20%, 1%-10%, 5%-80%, 5%-50%, 5%-30%, 5%-20%, 5%-10%, 10%-80%, 10%-50%, 10%-30%, 10%-20%, 20%-80%, 20%-50%, or 20%-30% native royalactin. Such a cosmetic product comprising purified royalactin as described herein can be a topical cosmetic product as described herein. It is contemplated that such cosmetic products comprising purified native royalactin in accordance with some embodiments herein can have biological activity such as stimulating colony formation and/or stimulating wound healing as described herein.

EXAMPLES

Example 1: Generation of a His-Tagged Royalactin Protein with Wound Healing Activity Bee (of the genus *Apis*) royal jelly had been reported in the past to enhance proliferation of some mammalian cells and enhance wound healing. Royalactin is one of the more abundant of the major royal jelly proteins, and the inventors hypothesized it might be responsible. The sequence of Royalactin protein was known and a bacterial fusion protein was made that included the full length royalactin protein with a histidine tag (SEQ ID NO: 4). This protein was purified by applying crude lysates to columns that had heavy metal ions linked to allow purification, and then used to treat cells in culture.

In vitro experiments to look at colony forming units were performed on U937 (human myeloid lineage) and HEK293 (human embryonic kidney) cell lines, and demonstrated increased colony formation in the presence of the purified protein. This result was also extended to embryonic stem cells, and a similar result was seen. Finally, the purified protein was used on an animal model of delayed wound healing, the diabetic (db/db) mouse. This showed the application of the protein resulted in an approximately 50% improvement in wound healing. Thus, the His-tagged royalactin protein (SEQ ID NO: 2) possessed biological activity for stimulating colony formation in multiple types of human cells, and in a mouse model of delayed wound healing.

Example 2: Generation of Antibody Directed at Royalactin

The fusion protein containing the full-length royalactin with a histidine tag (SEQ ID NO: 2), which was confirmed to have biological activity in Example 1, was produced in bacteria and purified. This protein was used to generate monoclonal antibodies by injection into mice with subsequent harvest of the spleen for generation of multiple hybridomas. Individual hybridomas were isolated and the antibody produced was screened using dot immunoblot assays. Various concentrations of royalactin were dotted onto the blot with bovine serum albumin (BSA) as a control. A total of 30 separate hybridomas were tested using the dot immunoblot assays (FIGS. 3A and 3B) and the 5 with the highest affinity for royalactin were selected for further analysis (hybridomas #19, 20, 21, 22, and 23).

The results of the Western dot blot are summarized in Table 1, below:

TABLE 1

| Result | Hybridoma No(s): |
|---|---|
| No RA Signal Detected: | #16 |
|  | #17 |
|  | #18 |
|  | #25 |
|  | #26 |
|  | #27 |
|  | #28 |
|  | #29 |
|  | #30 |
| Signal for 1.0 ng of RA: | #1 through #14 |
|  | #19 through #24 |
| Signal for 0.1 ng of RA: | #19 - 4G6C5 |
|  | #20 - 8C5C9 |
|  | #21 - 8C5D3 |
|  | #22 - 4G6E2 |
|  | #23 - 9G6A2 |
| Signal for 0.01 ng of RA: | None |
| Signal for 2 ng of BSA: | None |

Example 3: Immunoprecipitation of Protein by Antibody

Antibodies noted above that passed the initial screen were further tested for their ability to bind royalactin using an immunoprecipitation experiment. 500 ng of purified royalactin was incubated in varying amounts of the monoclonal antibodies being tested. After binding, protein A linked agarose beads were added to immunoprecipitate the antibody and bound protein. The precipitate was electrophoresed on SDS-PAGE gels to demonstrate that the protein being identified was the appropriate size and to partially quantify the amount of protein being bound. While all the antibodies were found to appropriately bind the protein, antibodies #19 and 20 had marginally better protein precipitation. As a result, monoclonal antibody #19 was chosen for further use in making an enriched extract from royal jelly.

Example 4: Ability of Conjugated Antibody to Bind Royalactin

Figure 4A:
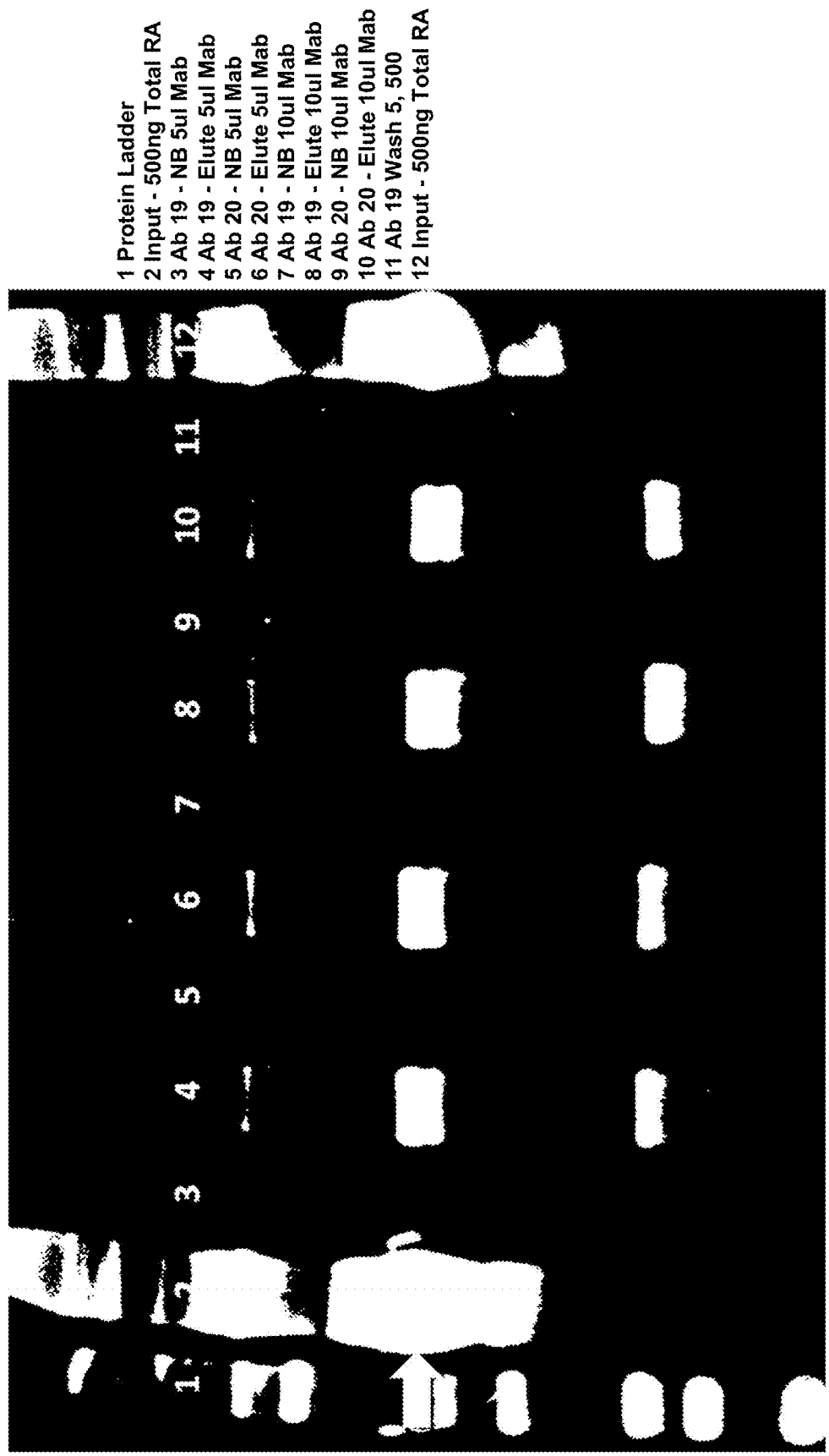
FIGS. 4A and 4B are images of Coomasie-stained gels for immunoprecipitation of royalactin by each of five monoclonal antibodies that bind to royalactin in accordance with some embodiments herein. The five antibodies (antibodies 19, 20, 21, 22, and 23) had been identified by immunoblotting as having the highest affinity for royalactin.
Figure 4B:
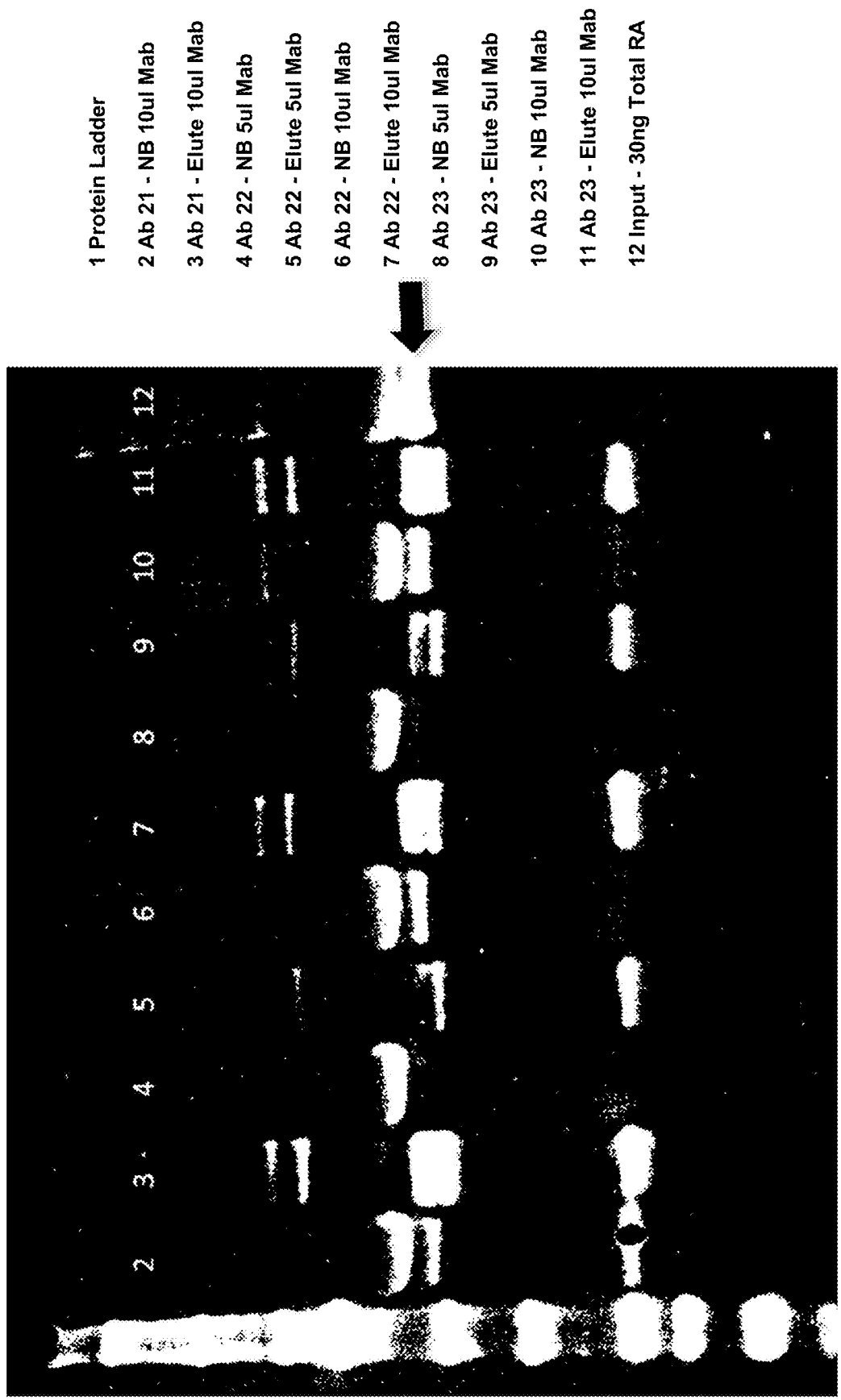

First, it was demonstrated the ability of the monoclonal antibodies to enrich for royalactin using the purified protein. Five monoclonal antibodies, antibodies 19 (4G6C5), 20 (8C5C9), 21 (8C5D3), 22 (4G6E2), and 23 (9G6A2) were tested. Varying amounts of the monoclonal antibody were conjugated to a bead support. After conjugation, a small amount of purified royalactin were incubated with the beads to allow for binding. The beads were then isolated and washed and the bound proteins analyzed by coomasie staining. The coomasie-stained gels are shown in FIGS. 4A and 4B. NB is flowthrough of IP. Elute is post IP fraction (retrieved sample). The band for royalactin are indicated by arrows (white arrow in FIG. 4A; black arrow in FIG. 4B).

This experiment demonstrated that the conjugated antibody was able to bind almost all of the royalactin protein as demonstrated by no detectable band in the wash while a strong band was present in the elute.

Example 5

Figure 5B:
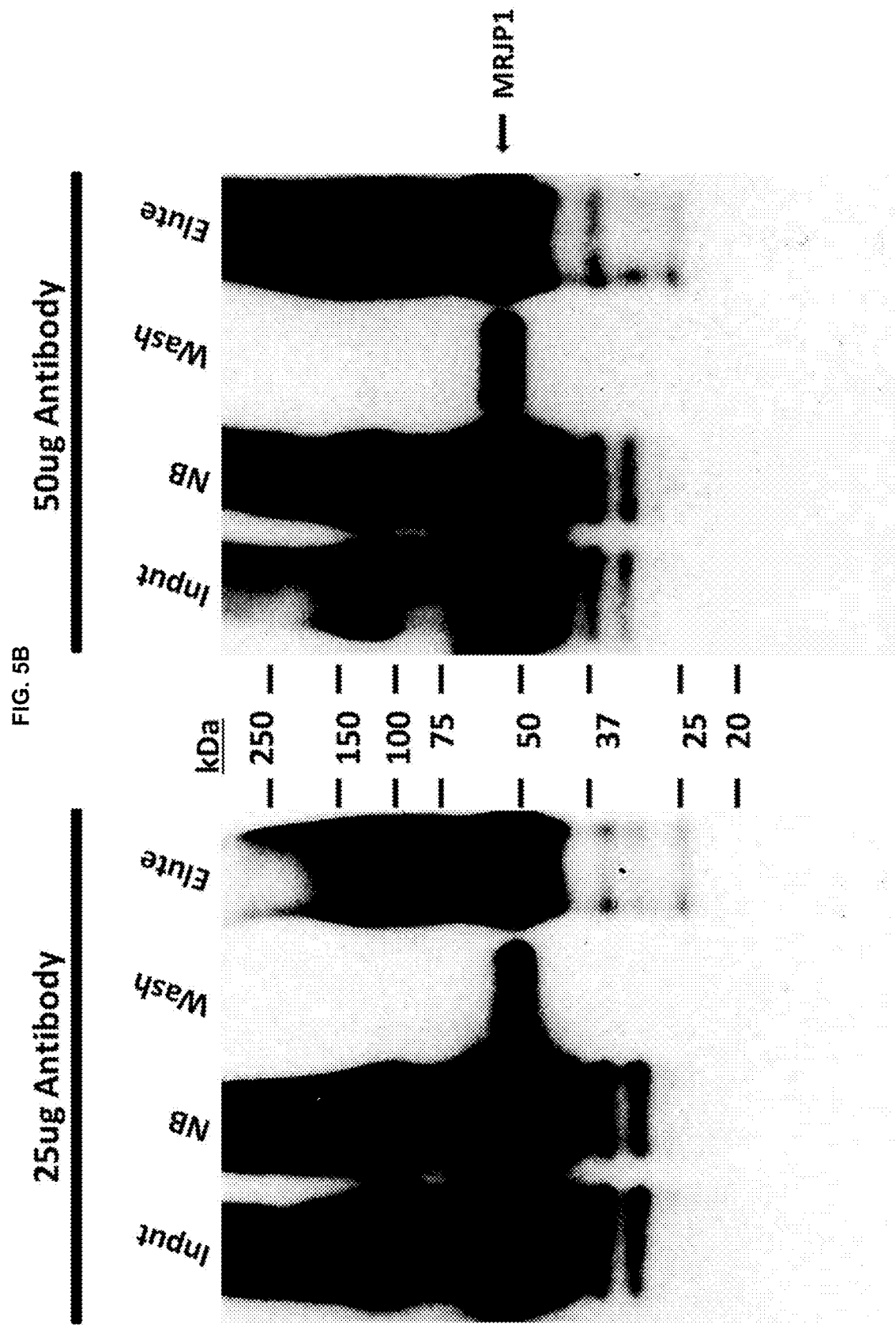
FIG. 5B is an image of a Western blot for RA on the input, NB, wash, and eluate of the immunoprecitpitation.

Sample enrichment scheme of royalactin. A small-scale experiment to demonstrate a protocol for enrichment of royalactin from royal jelly was performed. 1 g of royal jelly was dissolved in 34 ml of Tris pH7 buffer. Protein assay (BCA) of the mixture demonstrated a protein concentration of 3.22 mg/ml of total protein. Monoclonal antibody #19 (4G6C5) was conjugated to a Dynabead™ support. After conjugation, 1 mg of total royal jelly protein was added to the conjugated antibody and allowed to bind. The beads were then isolated and washed and the bound proteins separated on SDS-PAGE. This filter was then immunoblotted with antibody specific for royalactin to demonstrate the ability of the monoclonal antibody to significantly enrich for the appropriate sized band. The results are shown in FIG. 5A (Coomassie stained SGS-PAGE) and FIG. 5B (anti-RA western blot using polyclonal antibody against RA), and confirm that the protein in the size band corresponding to royalactin was enriched.

Example 6

The nucleic acids encoding the HCVR and the LCVR of monoclonal antibody #19 (4G6C5) according to some embodiments were sequenced. The nucleic acid encoding the HCVR (SEQ ID NO: 5) is shown in FIG. 6A and the corresponding translated HCVR polypeptide (SEQ ID NO: 6) is shown in FIG. 6B. The nucleic acid encoding the LCVR (SEQ ID NO: 7) is shown in FIG. 6C and the corresponding translated LCVR polypeptide (SEQ ID NO: 8) is shown in FIG. 6D.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. One skilled in the art will appreciate that, for this and other processes and methods disclosed herein, the functions performed in the processes and methods can be implemented in differing order. Furthermore, the outlined steps and operations are only provided as examples, and some of the steps and operations can be optional, combined into fewer steps and operations, or expanded into additional steps and operations without detracting from the essence of the disclosed embodiments.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "an antibody having at least one of A, B, and C" would include but not be limited to antibody that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "an antibody having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A method for purifying native royalactin, the method comprising:
   solubilizing a biological matter comprising native royalactin in an aqueous solution,
   contacting the aqueous solution comprising the solubilized biological matter with a monoclonal antibody immobilized on a substrate, wherein the monoclonal antibody binds specifically to the amino acid sequence of SEQ ID NO: 2, thereby binding the monoclonal antibody to the native royalactin;
   separating the monoclonal antibody bound to native royalactin from the aqueous solution; and
   removing the bound native royalactin from the monoclonal antibody, thereby purifying native royalactin,
   wherein the monoclonal antibody comprises:
      a HCVR of the HCVR of SEQ ID NO: 6; and
      a LCVR of the LCVR of SEQ ID NO: 8.

2. The method of claim 1, wherein the monoclonal antibody comprises:
   a heavy chain variable region (HCVR) having a CDR3 domain of the CDR3 domain of SEQ ID NO: 6, a CDR2 domain of the CDR2 domain of SEQ ID NO: 6, and a CDR1 domain of the CDR1 domain of SEQ ID NO: 6, and a light chain variable region (LCVR) having a CDR3 domain of the CDR3 domain of SEQ ID NO: 8, a CDR2 domain of the CDR2 domain of SEQ ID NO: 8, and a CDR1 domain of the CDR1 domain of SEQ ID NO: 8.

3. The method of claim 1, wherein the monoclonal antibody competes for binding with:
   an other monoclonal antibody comprising a heavy chain variable region (HCVR) having a CDR3 domain of the CDR3 domain of SEQ ID NO: 6, a CDR2 domain of the CDR2 domain of SEQ ID NO: 6, and a CDR1 domain of the CDR1 domain of SEQ ID NO: 6, and a light chain variable region (LCVR) having a CDR3 domain of the CDR3 domain of SEQ ID NO: 8, a CDR2 domain of the CDR2 domain of SEQ ID NO: 8, and a CDR1 domain of the CDR1 domain of SEQ ID NO: 8.

4. The method of claim 1, further comprising preparing a composition comprising purified native royalactin, wherein the composition comprises lyophilized native royalactin, or wherein the composition is comprised by a topical cosmetic product comprising the purified native royalactin.

5. The method of claim 1, wherein removing the bound native royalactin from the monoclonal antibody is performed by elution.

6. A method for purifying native royalactin, the method comprising:
   solubilizing a biological matter comprising native royalactin in an aqueous solution,
   contacting the aqueous solution comprising the solubilized biological matter with a monoclonal antibody immobilized on a substrate, wherein the monoclonal antibody binds specifically to the amino acid sequence of SEQ ID NO: 2, thereby binding the monoclonal antibody to the native royalactin;
   separating the monoclonal antibody bound to native royalactin from the aqueous solution; and
   removing the bound native royalactin from the monoclonal antibody, thereby purifying native royalactin,
   wherein the monoclonal antibody comprises:
      a heavy chain variable region (HCVR) comprising:
         a CDR3 domain of the CDR3 domain of SEQ NO: 6;
         a CDR2 domain of the CDR2 domain of SEQ NO: 6; and
         a CDR1 domain of the CDR1 domain of SEQ NO: 6; and
      a light chain variable region (LCVR) comprising:
         a CDR3 domain of the CDR3 domain of SEQ NO: 8;
         a CDR2 domain of the CDR2 domain of SEQ NO: 8; and
         a CDR1 domain of the CDR1 domain of SEQ NO: 8.

7. An isolated monoclonal antibody that binds specifically to royalactin, said monoclonal antibody comprising:
   a heavy chain variable region (HCVR) having a CDR3 domain of the CDR3 domain of SEQ ID NO: 6, a CDR2 domain of the CDR2 domain of SEQ ID NO: 6, and a CDR1 domain of the CDR1 domain of SEQ ID NO: 6, and a light chain variable region (LCVR) having a CDR3 domain of the CDR3 domain of SEQ ID NO: 8, a CDR2 domain of the CDR2 domain of SEQ ID NO: 8, and a CDR1 domain of the CDR1 domain of SEQ ID NO: 8, wherein the isolated monoclonal antibody comprises:
  a HCVR of the HCVR of SEQ ID NO: 6; and
  a LCVR of the LCVR of SEQ ID NO: 8.

8. An isolated monoclonal antibody that binds specifically to royalactin, said monoclonal antibody comprising:
  a heavy chain variable region (HCVR) comprising:
  a CDR3 domain of the CDR3 domain of SEQ NO: 6;
  a CDR2 domain of the CDR2 domain of SEQ NO: 6; and
  a CDR1 domain of the CDR1 domain of SEQ NO: 6; and
  a light chain variable region (LCVR) comprising:
  a CDR3 domain of the CDR3 domain of SEQ NO: 8;
  a CDR2 domain of the CDR2 domain of SEQ NO: 8; and
  a CDR1 domain of the CDR1 domain of SEQ NO: 8.

9. An isolated nucleic acid that encodes an isolated monoclonal antibody according to claim 7, wherein the monoclonal antibody comprises:
  a (HCVR) comprising: a CDR3 domain of the CDR3 domain of SEQ NO: 6; a CDR2 domain of the CDR2 domain of SEQ NO: 6; and a CDR1 domain of the CDR1 domain of SEQ NO: 6; and
  a light chain variable region (LCVR) comprising: a CDR3 domain of the CDR3 domain of SEQ NO: 8; a CDR2 domain of the CDR2 domain of SEQ NO: 8; and a CDR1 domain of the CDR1 domain of SEQ NO: 8.

10. The isolated nucleic acid of claim 9, wherein the isolated nucleic acid comprises SEQ NO: 3 and SEQ ID NO: 5, wherein SEQ ID NO: 3 and SEQ ID NO: 5 are comprised by the same polynucleotide, or are comprised by different polynucleotides.

* * * * *

SEQUENCE LISTING

<160> NUMBER OF SEQ ID NOS: 8

<210> SEQ ID NO 1
<211> LENGTH: 1299
<212> TYPE: DNA
<213> ORGANISM: Apis melifera
<220> FEATURE:
<221> NAME/KEY: misc_feature
<222> LOCATION: 1089
<223> OTHER INFORMATION: n = A,T,C or G

<400> SEQUENCE: 1

| | | | | | | |
|---|---|---|---|---|---|---|
| atgacaagat | tgtttatgct | ggtatgcctt | ggcatagttt | gtcaaggtac | gacaggcaac | 60 |
| attcttcgag | gagagtcttt | aaacaaatca | ttacccatcc | ttcacgaatg | gaaattcttt | 120 |
| gattatgatt | tcggtagcga | tgaaagaaga | caagatgcaa | ttctatctgg | cgaatacgac | 180 |
| tacaagaata | attatccatc | cgacattgac | caatggcatg | ataagatttt | tgtcaccatg | 240 |
| ctgagataca | atggcgtacc | ttcctctttg | aacgtgatat | ctaaaaaggt | cggtgatggt | 300 |
| ggtcctcttc | tacaacctta | tcccgattgg | tcgtttgcta | aatatgacga | ttgctctgga | 360 |
| atcgtgagcg | cctcaaaact | tgcgatcgac | aaatgcgaca | gattgtgggt | tctggactca | 420 |
| ggtcttgtca | ataatactca | acccatgtgt | tctccaaaac | tgctcacctt | tgatctgact | 480 |
| acctcgcaat | tgctcaagca | agttgaaata | ccacatgatg | ttgccgtaaa | tgccactaca | 540 |
| ggaaagggaa | gattatcatc | tctagctgtt | caatctttag | attgcaatac | aaatagcgat | 600 |
| actatggtgt | acatagcaga | cgagaaaggt | gaaggtttaa | tcgtgtatca | taattctgat | 660 |
| gattccttcc | atcgattgac | ttccaacact | ttcgattacg | atcctaaatt | taccaaaatg | 720 |
| acgatcgatg | gagaaagtta | cacagcccaa | gatggaattt | ctggaatggc | tcttagtccc | 780 |
| atgactaaca | atctctatta | cagtcctgta | gcttccacca | gtttgtatta | tgttaacacg | 840 |
| gaacaattca | gaacatccga | ttatcaacag | aatgacatac | attacgaagg | agtccaaaat | 900 |
| attttggata | cccaatcgtc | cgctaaagta | gtatcaaaga | gtggcgttct | cttcttcgga | 960 |
| ttggtgggcg | attcagctct | tggctgctgg | aacgaacatc | gaacacttga | aagacacaat | 1020 |
| atccgtaccg | tcgctcaaag | tgatgagact | cttcaaatga | tcgctagcat | gaagattaag | 1080 |
| gaagctctnc | cacacgtgcc | tatattcgat | aggtatataa | accgtgaata | catattggtt | 1140 |
| ttaagtaaca | aaatgcaaaa | aatggtgaat | aatgacttca | acttcgacga | tgttaacttc | 1200 |
| agaattatga | acgcgaatgt | aaacgaattg | atattgaaca | ctcgttgcga | aaatcccgat | 1260 |
| aatgatcgaa | cacctttcaa | aatttcaatc | catttgtaa | | | 1299 |

<210> SEQ ID NO 2
<211> LENGTH: 432
<212> TYPE: PRT
<213> ORGANISM: Apis melifera
<220> FEATURE:
<221> NAME/KEY: VARIANT
<222> LOCATION: 363
<223> OTHER INFORMATION: Xaa = Any Amino Acid

<400> SEQUENCE: 2

```
Met Thr Arg Leu Phe Met Leu Val Cys Leu Gly Ile Val Cys Gln Gly
1               5                   10                  15

Thr Thr Gly Asn Ile Leu Arg Gly Glu Ser Leu Asn Lys Ser Leu Pro
            20                  25                  30

Ile Leu His Glu Trp Lys Phe Phe Asp Tyr Asp Phe Gly Ser Asp Glu
        35                  40                  45

Arg Arg Gln Asp Ala Ile Leu Ser Gly Glu Tyr Asp Tyr Lys Asn Asn
    50                  55                  60

Tyr Pro Ser Asp Ile Asp Gln Trp His Asp Lys Ile Phe Val Thr Met
65                  70                  75                  80

Leu Arg Tyr Asn Gly Val Pro Ser Ser Leu Asn Val Ile Ser Lys Lys
                85                  90                  95

Val Gly Asp Gly Gly Pro Leu Leu Gln Pro Tyr Pro Asp Trp Ser Phe
            100                 105                 110

Ala Lys Tyr Asp Asp Cys Ser Gly Ile Val Ser Ala Ser Lys Leu Ala
        115                 120                 125

Ile Asp Lys Cys Asp Arg Leu Trp Val Leu Asp Ser Gly Leu Val Asn
    130                 135                 140

Asn Thr Gln Pro Met Cys Ser Pro Lys Leu Leu Thr Phe Asp Leu Thr
145                 150                 155                 160

Thr Ser Gln Leu Leu Lys Gln Val Glu Ile Pro His Asp Val Ala Val
                165                 170                 175

Asn Ala Thr Thr Gly Lys Gly Arg Leu Ser Ser Leu Ala Val Gln Ser
            180                 185                 190

Leu Asp Cys Asn Thr Asn Ser Asp Thr Met Val Tyr Ile Ala Asp Glu
        195                 200                 205

Lys Gly Glu Gly Leu Ile Val Tyr His Asn Ser Asp Ser Phe His
    210                 215                 220

Arg Leu Thr Ser Asn Thr Phe Asp Tyr Asp Pro Lys Phe Thr Lys Met
225                 230                 235                 240

Thr Ile Asp Gly Glu Ser Tyr Thr Ala Gln Asp Gly Ile Ser Gly Met
                245                 250                 255

Ala Leu Ser Pro Met Thr Asn Asn Leu Tyr Tyr Ser Pro Val Ala Ser
            260                 265                 270

Thr Ser Leu Tyr Tyr Val Asn Thr Glu Gln Phe Arg Thr Ser Asp Tyr
        275                 280                 285

Gln Gln Asn Asp Ile His Tyr Glu Gly Val Gln Asn Ile Leu Asp Thr
    290                 295                 300

Gln Ser Ser Ala Lys Val Val Ser Lys Ser Gly Val Leu Phe Phe Gly
305                 310                 315                 320

Leu Val Gly Asp Ser Ala Leu Gly Cys Trp Asn Glu His Arg Thr Leu
                325                 330                 335

Glu Arg His Asn Ile Arg Thr Val Ala Gln Ser Asp Gly Thr Leu Gln
            340                 345                 350

Met Ile Ala Ser Met Lys Ile Lys Glu Ala Xaa Pro His Val Pro Ile
        355                 360                 365

Phe Asp Arg Tyr Ile Asn Arg Glu Tyr Ile Leu Val Leu Ser Asn Lys
    370                 375                 380

Met Gln Lys Met Val Asn Asn Asp Phe Asn Phe Asp Asp Val Asn Phe
385                 390                 395                 400

Arg Ile Met Asn Ala Asn Val Asn Glu Leu Ile Leu Asn Thr Arg Cys
```

405                 410                 415
Glu Asn Pro Asp Asn Asp Arg Thr Pro Phe Lys Ile Ser Ile His Leu
                420                 425                 430

<210> SEQ ID NO 3
<211> LENGTH: 1353
<212> TYPE: DNA
<213> ORGANISM: Artificial Sequence
<220> FEATURE:
<223> OTHER INFORMATION: Coding sequence for Flag-Royalactin-His fusion
      protein

<400> SEQUENCE: 3
atggaatgga gctgggtctt tctcttcttc ctgtcagtaa cgactggtgt ccactccgat    60
tacaaggacg acgatgacaa gaacattctg cgtggggaat ccctgaacaa gtcattgcct   120
atccttcatg aatggaaatt cttttgattat gattttggtt ccgacgaacg acggcaggac   180
gccatcctct ctggagaata tgattacaaa acaactacc cttctgatat cgaccagtgg   240
cacgataaga ttttttgtcac catgctgcgg tacaatggag ttccctcttc actgaacgtc   300
atcagtaaga aggtgggcga cggaggaccc ctgctccagc catatcctga ttggtctttc   360
gctaagtacg acgactgttc tggaatcgtc tccgcttcta agctggccat tgacaagtgt   420
gatcggttgt gggtcctgga ttcagggttg gtgaacaata cccagcccat gtgctctcct   480
aagctgctga ccttcgacct caccaccagc cagttgctca gcaggtgga gattccccac   540 gacgtcgctg tgaacgctac cacaggcaag ggccgcttga gcagccttgc tgtgcaaagc   600
ctggactgca acaccaattc agatactatg gtgtacatcg cagacgaaaa gggtgaaggt   660
ctgattgtct accataactc agacgatagt tttcatagac tgacctccaa cacattcgat   720
tatgacccca gttcactaa gatgactatt gacggtgagt catacactgc ccaggacggg   780
atttccggta tggcactgtc acctatgaca aataacctgt attattctcc cgttgcaagc   840
acttctctgt actacgtgaa cactgagcaa ttcaggacca gcgactatca acagaatgat   900
atccattacg agggagtcca gaacatcctt gacactcagt cctctgccaa ggtagttagc   960
aagagtggag tattgttttt cggcctggtt ggcgacagtg ctttgggatg ttggaatgaa  1020
catcggaccc tggaacgtca taacattcgc actgtggccc aatctgacga gactcttcag  1080
atgatcgcct ctatgaagat aaaggaggcc ttgccccacg tccctatctt cgacaggtat  1140
atcaaccgtg aatatatact ggtgctctca ataagatgc agaaaatggt taataatgat  1200
ttcaattttg acgatgtgaa ttttaggatc atgaacgcaa acgttaatga actgatcttg  1260
aatacccgtt gtgagaatcc cgacaacgat aggacaccct taagatttc tattcacctg  1320 caccaccatc atcaccatca ccaccatcac tag                                1353

<210> SEQ ID NO 4
<211> LENGTH: 450
<212> TYPE: PRT
<213> ORGANISM: Artificial Sequence
<220> FEATURE:
<223> OTHER INFORMATION: Flag-Royalactin-His fusion protein

<400> SEQUENCE: 4

Met Glu Trp Ser Trp Val Phe Leu Phe Phe Leu Ser Val Thr Thr Gly
1               5                   10                  15

Val His Ser Asp Tyr Lys Asp Asp Asp Asp Lys Asn Ile Leu Arg Gly
            20                  25                  30

Glu Ser Leu Asn Lys Ser Leu Pro Ile Leu His Glu Trp Lys Phe Phe

```
                    35                  40                  45
Asp Tyr Asp Phe Gly Ser Asp Glu Arg Arg Gln Asp Ala Ile Leu Ser
 50                  55                  60
Gly Glu Tyr Asp Tyr Lys Asn Asn Tyr Pro Ser Asp Ile Asp Gln Trp
 65                  70                  75                  80
His Asp Lys Ile Phe Val Thr Met Leu Arg Tyr Asn Gly Val Pro Ser
                     85                  90                  95
Ser Leu Asn Val Ile Ser Lys Lys Val Gly Asp Gly Gly Pro Leu Leu
                    100                 105                 110
Gln Pro Tyr Pro Asp Trp Ser Phe Ala Lys Tyr Asp Asp Cys Ser Gly
                    115                 120                 125
Ile Val Ser Ala Ser Lys Leu Ala Ile Asp Lys Cys Asp Arg Leu Trp
                    130                 135                 140
Val Leu Asp Ser Gly Leu Val Asn Asn Thr Gln Pro Met Cys Ser Pro
145                 150                 155                 160
Lys Leu Leu Thr Phe Asp Leu Thr Thr Ser Gln Leu Leu Lys Gln Val
                    165                 170                 175
Glu Ile Pro His Asp Val Ala Val Asn Ala Thr Thr Gly Lys Gly Arg
                    180                 185                 190
Leu Ser Ser Leu Ala Val Gln Ser Leu Asp Cys Asn Thr Asn Ser Asp
                    195                 200                 205
Thr Met Val Tyr Ile Ala Asp Glu Lys Gly Glu Gly Leu Ile Val Tyr
210                 215                 220
His Asn Ser Asp Asp Ser Phe His Arg Leu Thr Ser Asn Thr Phe Asp
225                 230                 235                 240
Tyr Asp Pro Lys Phe Thr Lys Met Thr Ile Asp Gly Glu Ser Tyr Thr
                    245                 250                 255
Ala Gln Asp Gly Ile Ser Gly Met Ala Leu Ser Pro Met Thr Asn Asn
                    260                 265                 270
Leu Tyr Tyr Ser Pro Val Ala Ser Thr Ser Leu Tyr Tyr Val Asn Thr
                    275                 280                 285
Glu Gln Phe Arg Thr Ser Asp Tyr Gln Gln Asn Asp Ile His Tyr Glu
                    290                 295                 300
Gly Val Gln Asn Ile Leu Asp Thr Gln Ser Ser Ala Lys Val Val Ser
305                 310                 315                 320
Lys Ser Gly Val Leu Phe Phe Gly Leu Val Gly Asp Ser Ala Leu Gly
                    325                 330                 335
Cys Trp Asn Glu His Arg Thr Leu Glu Arg His Asn Ile Arg Thr Val
                    340                 345                 350
Ala Gln Ser Asp Glu Thr Leu Gln Met Ile Ala Ser Met Lys Ile Lys
                    355                 360                 365
Glu Ala Leu Pro His Val Pro Ile Phe Asp Arg Tyr Ile Asn Arg Glu
                    370                 375                 380
Tyr Ile Leu Val Leu Ser Asn Lys Met Gln Lys Met Val Asn Asn Asp
385                 390                 395                 400
Phe Asn Phe Asp Asp Val Asn Phe Arg Ile Met Asn Ala Asn Val Asn
                    405                 410                 415
Glu Leu Ile Leu Asn Thr Arg Cys Glu Asn Pro Asp Asn Asp Arg Thr
                    420                 425                 430
Pro Phe Lys Ile Ser Ile His Leu His His His His His His His His
                    435                 440                 445
His His
450
```

<210> SEQ ID NO 5
<211> LENGTH: 339
<212> TYPE: DNA
<213> ORGANISM: Mus musculus

<400> SEQUENCE: 5

```
gtgatgctgg tggaatctgg gggaggctta gtgaagcctg gagggtccct gaaactctcc      60
tgtgcagcct ctggattcac tttcagtagg tatgccatgt cttggaatcg ccagactccg     120
gagaagaggc tggagtgggt cgcaacaatt agtcctggtg gtggttacat atactattca     180
gacagtgtga aggggcgatt caccatctcc agagacaatg ccaggaacac cctgtatctg     240
caaatgagca gtctgaggtc tgaggacacg gccatgtatt actgtgcagg ggactatgtt     300
gactattggg gccaaggcac cactctcaca gtctcctca                            339
```

<210> SEQ ID NO 6
<211> LENGTH: 113
<212> TYPE: PRT
<213> ORGANISM: Mus musculus

<400> SEQUENCE: 6

Val Met Leu Val Glu Ser Gly Gly Gly Leu Val Lys Pro Gly Gly Ser
1               5                  10                  15

Leu Lys Leu Ser Cys Ala Ala Ser Gly Phe Thr Phe Ser Arg Tyr Ala
            20                  25                  30

Met Ser Trp Asn Arg Gln Thr Pro Glu Lys Arg Leu Glu Trp Val Ala
        35                  40                  45

Thr Ile Ser Pro Gly Gly Gly Tyr Ile Tyr Tyr Ser Asp Ser Val Lys
    50                  55                  60

Gly Arg Phe Thr Ile Ser Arg Asp Asn Ala Arg Asn Thr Leu Tyr Leu
65                  70                  75                  80

Gln Met Ser Ser Leu Arg Ser Glu Asp Thr Ala Met Tyr Tyr Cys Ala
                85                  90                  95

Gly Asp Tyr Val Asp Tyr Trp Gly Gln Gly Thr Thr Leu Thr Val Ser
            100                 105                 110

Ser

<210> SEQ ID NO 7
<211> LENGTH: 339
<212> TYPE: DNA
<213> ORGANISM: Mus musculus

<400> SEQUENCE: 7

```
gatgttgtga tgacccagac tccactcact ttgtcggtta ccactggaca accagcctcc      60
atctcttgca agtcaagtca gagcctctta aatagtgatg aaagacatt tttgaattgg      120 ttgttacaga ggccagggca gtctccaaag cgcctaatct atctggtgtc taaactggac     180
tctggagtcc ctgacaggtt cactggcagt ggatcaggga cagatttcac actgaaaatc     240
agcagagtgg aggctgagga tttgggagtt tattattgct ggcaaggtac acattttcca     300
tacacgttcg gaggggggac caagctggaa ataaaacgg                            339
```

<210> SEQ ID NO 8
<211> LENGTH: 113
<212> TYPE: PRT
<213> ORGANISM: Mus musculus

<400> SEQUENCE: 8

```
Asp Val Val Met Thr Gln Thr Pro Leu Thr Leu Ser Val Thr Thr Gly
 1               5                  10                 15

Gln Pro Ala Ser Ile Ser Cys Lys Ser Ser Gln Ser Leu Leu Asn Ser
            20                  25                  30

Asp Gly Lys Thr Phe Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
        50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Tyr Thr Phe Gly Gly Gly Thr Lys Leu Glu Ile Lys
                100                 105                 110

Arg
```